US012569153B2

(12) United States Patent
Huber et al.

(10) Patent No.: US 12,569,153 B2
(45) Date of Patent: Mar. 10, 2026

(54) SYSTEM AND APPARATUS FOR MEASUREMENT OF PHYSIOLOGICAL DATA

(71) Applicant: Radio Systems Corporation, Knoxville, TN (US)

(72) Inventors: Jonathan Huber, Knoxville, TN (US); Kevin Michael Sayers, Knoxville, TN (US); Richard Seltzer, Knoxville, TN (US)

(73) Assignee: Radio Systems Corporation, Knoxville, TN (US)

( * ) Notice: Subject to any disclaimer, the term of this patent is extended or adjusted under 35 U.S.C. 154(b) by 835 days.

(21) Appl. No.: 17/673,215

(22) Filed: Feb. 16, 2022

(65) Prior Publication Data

US 2022/0257132 A1     Aug. 18, 2022

Related U.S. Application Data

(60) Provisional application No. 63/149,936, filed on Feb. 16, 2021.

(51) Int. Cl.
*A01K 27/00* (2006.01)
*A61B 5/00* (2006.01)
(Continued)

(52) U.S. Cl.
CPC ............ *A61B 5/02433* (2013.01); *A61B 5/01* (2013.01); *A61B 5/6802* (2013.01); (Continued)

(58) Field of Classification Search
CPC ........................ A61B 5/02438; A61B 2503/40
See application file for complete search history.

(56) References Cited

U.S. PATENT DOCUMENTS

2009/0149727 A1     6/2009 Truitt et al.
2012/0073517 A1     3/2012 Dukes
(Continued)

OTHER PUBLICATIONS

International Search Report and Written Opinion for Application No. PCT/US2022/016588, dated May 11, 2022, 12 pages.
(Continued)

*Primary Examiner* — Joshua J Michener
*Assistant Examiner* — Henry Hooper Mudd
(74) *Attorney, Agent, or Firm* — Baker, Donelson, Bearman, Caldwell & Berkowitz, PC

(57)     ABSTRACT

A collar device is described herein comprising a housing including an emitter and a detector, wherein a base of the housing exposes the emitter and the detector. A spacer component comprising a plurality of optical pathways, wherein the plurality of optical pathways comprises a first optical pathway and a second optical pathway. The spacer component is secured to the base of the housing, wherein the first optical pathway is positioned over an emitter, wherein the second optical pathway is positioned over a detector. The emitter is configured to project light through the first optical pathway toward skin tissue of an animal. The detector is configured to detect portions of the light reflected by the skin tissue back through the second optical pathway. One or more applications running on at least one processor are configured to receive information of the reflected light and use the information to determine a biological metric.

25 Claims, 23 Drawing Sheets

(51) Int. Cl.
   *A61B 5/01* (2006.01)
   *A61B 5/024* (2006.01)

(52) U.S. Cl.
   CPC .... *A61B 5/6822* (2013.01); *A61B 2562/0233* (2013.01); *A61B 2562/0271* (2013.01)

(56) References Cited

U.S. PATENT DOCUMENTS

| | | | |
|---|---|---|---|
| 2015/0141772 A1 | 5/2015 | LeBoeuf et al. | |
| 2015/0181840 A1 | 7/2015 | Tupin, Jr. et al. | |
| 2016/0367187 A1 | 12/2016 | Ahmed | |
| 2017/0095206 A1 | 4/2017 | Leib | |
| 2017/0325698 A1* | 11/2017 | Allec | A61B 5/026 |
| 2018/0000353 A1 | 1/2018 | Thieme et al. | |
| 2019/0069786 A1 | 3/2019 | Perez-Camargo | |
| 2019/0086331 A1 | 3/2019 | Han et al. | |
| 2020/0267936 A1 | 8/2020 | Tran | |
| 2021/0045671 A1* | 2/2021 | Wiese | A61B 5/1455 |
| 2022/0104464 A1 | 4/2022 | Wernimont | |
| 2023/0240591 A1* | 8/2023 | De Bock | A61B 5/00 |
| 2023/0389832 A1* | 12/2023 | Li | A61B 5/145 |

OTHER PUBLICATIONS

International Search Report and Written Opinion for Application No. PCT/US2023/014890, dated Jun. 27, 2023, 7 pages.

* cited by examiner

SYSTEM AND APPARATUS FOR MEASUREMENT OF PHYSIOLOGICAL DATA

RELATED APPLICATIONS

This application claims the benefit of U.S. Application No. 63/149,936, filed Feb. 16, 2021.

TECHNICAL FIELD

The disclosure herein involves a collar device for measuring physiological data.

BACKGROUND

There is an interest in tracking biometric data of pet animals. There is a need for a wearable device which tracks such animal data in real time.

INCORPORATION BY REFERENCE

Each patent, patent application, and/or publication mentioned in this specification is herein incorporated by reference in its entirety to the same extent as if each individual patent, patent application, and/or publication was specifically and individually indicated to be incorporated by reference.

DETAILED DESCRIPTION

There is interest among dog owners in monitoring the biometrics of canines. Whether dealing with working animals, outdoor adventure animals, or around the house pets, there is a persistent consumer desire to know if a pet is healthy. There are products that measure heart rate in animals via a microphone placed on the artery cluster on a dog's neck. This method is fine for a steady-state measurement on a dormant animal but is not effective during activity. A device is described herein to track the heart rate of these animals at both normal and elevated activity levels.

In humans, the electrocardiography (ECG) is utilized on exercise equipment, wearables, etc. However, this technology presents a problem when worn by an animal. For an ECG device, the oils on animals differ from those of humans, and hence, the electrical connection needed to detect a heartbeat effectively is not present. Also, ECG requires a motionless subject. Accordingly, the technology fails in the presence of motion.

Photoplethysmography (PPG) detection is a noninvasive method of measuring the heart rate by monitoring changes in blood volume in the microvascular bed of skin tissue due to heart beats. The PPG method works by emitting a light from a light source into the skin from the skin surface and then by detecting the amount of light returned to a photodetector, also aimed into the skin from the surface. A majority of the light emitted into the skin is absorbed by the body tissue. However, some of the light is reflected and picked up by the photodetector. As blood absorbs light more efficiently than the surrounding tissue, the pressure pulses of arterial and venous blood flow are detectable as a slight change in this reflected light. If an air gap exists between the light emitter/photo-detector and skin surface, the surface reflection is also picked up by the detector, making the change due to blood flow even smaller. This value of light reflection change due to blood flow (AC) versus the steady state light reflection due to tissue and surface reflections (DC) is referred to as the Perfusion Index (PI).

The perfusion index (PI) is the ratio between the variable pulsatile (AC) and nonpulsatile (DC) signals and is an indirect and noninvasive measurement of peripheral perfusion. It is calculated by means of pulse oximetry by expressing the pulsatile signal (during arterial flow) as a percentage of the nonpulsatile signal. Accordingly, PI is computed as AC/DC*100.

Figure 1:
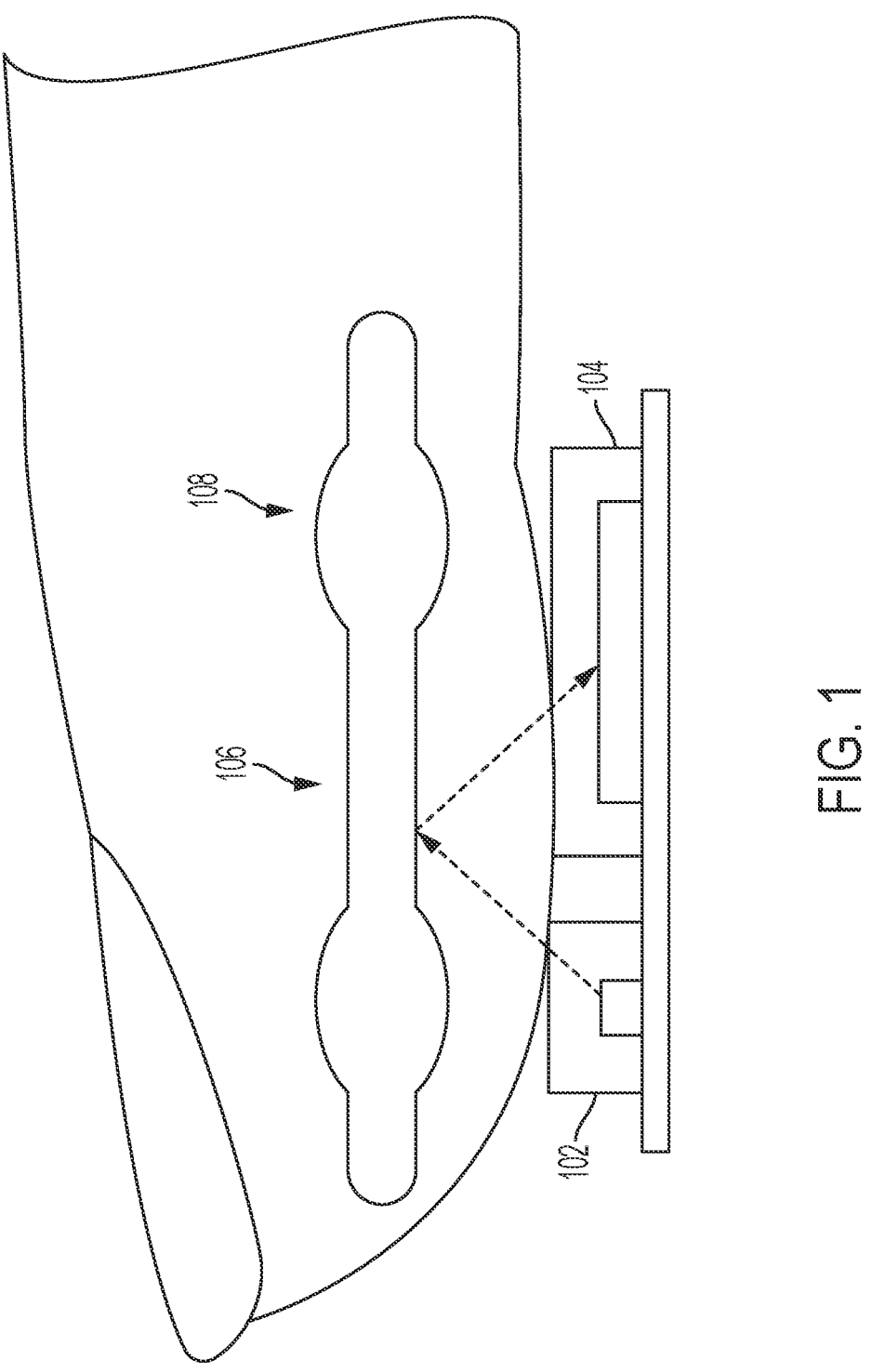
FIG. 1 shows a model for detecting and monitoring a PPG signal in humans, under an embodiment.

FIG. 1 shows a model for detecting and monitoring a PPG signal in humans, under an embodiment. FIG. 1 shows blood flow (diastolic 106 and systolic 108 points). An LED light or other light emitter 102 directs light into a finger. A portion of the light is absorbed by the finger while a portion of the light is reflected. The photo detector (e.g. photo diode) 104 detects reflected portions. Accordingly, information of absorbed light and reflected light may then be used to compute PI in real time.

Figure 2:
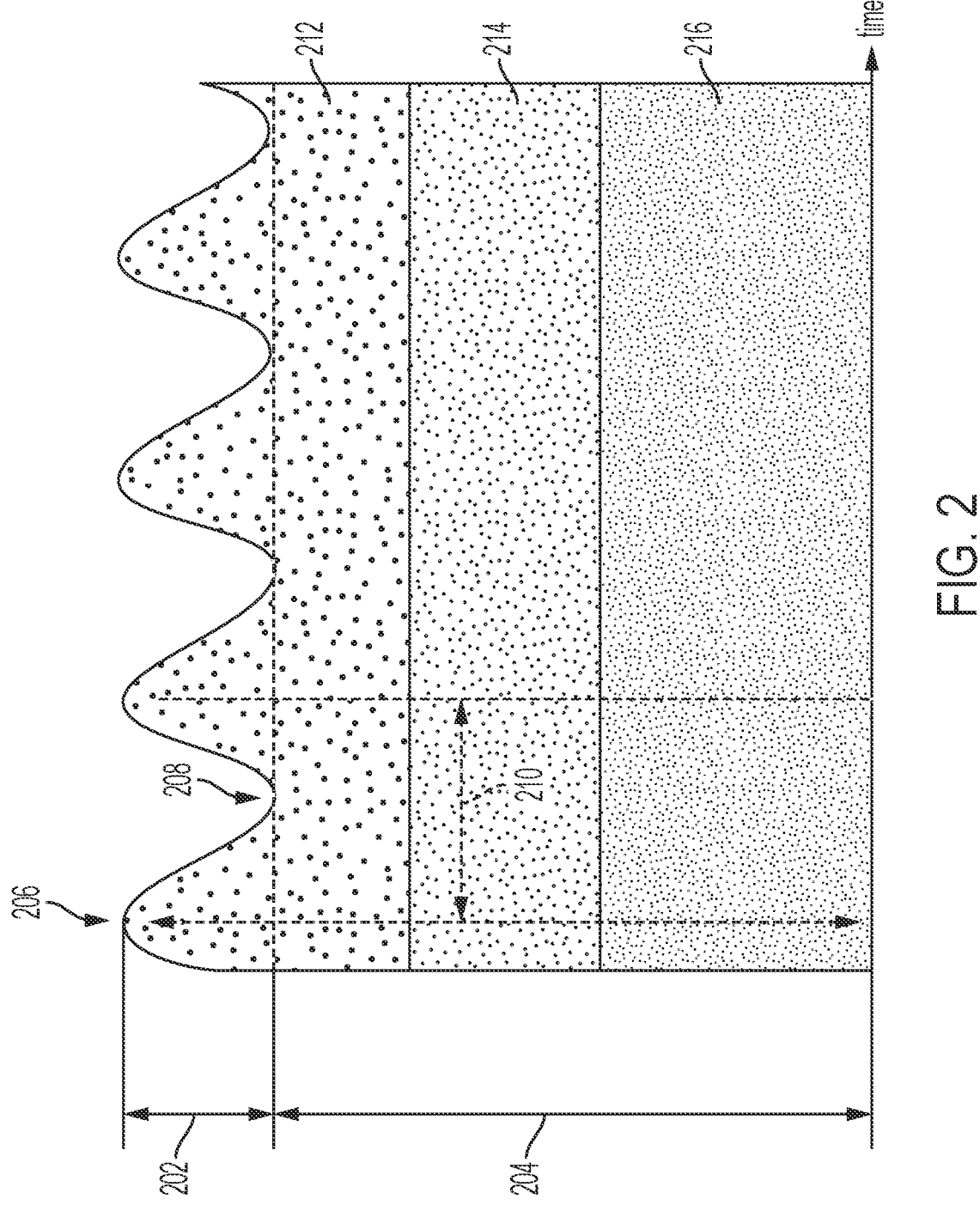
FIG. 2 show blood flow changes as a waveform, under an embodiment.

PPG shows the blood flow changes as a waveform with the help of a bar or a graph as seen in FIG. 2. The waveform has an alternating current (AC) component 202 and a direct current (DC) component 204. The AC component corresponds to variations in blood volume in synchronization with the heartbeat. FIG. 2 shows an AC signal over time corresponding to pulsatile arterial blood. FIG. 2 illustrates systolic 206 and diastolic 208 points of contraction (as further defined below) and identifies a cardiac cycle 210 as the time between successive systolic points. The DC component is attributed to the light absorption of non-pulsatile arterial blood 212, venous blood 214, and tissue 216 as also shown in FIG. 2.

Figure 3:
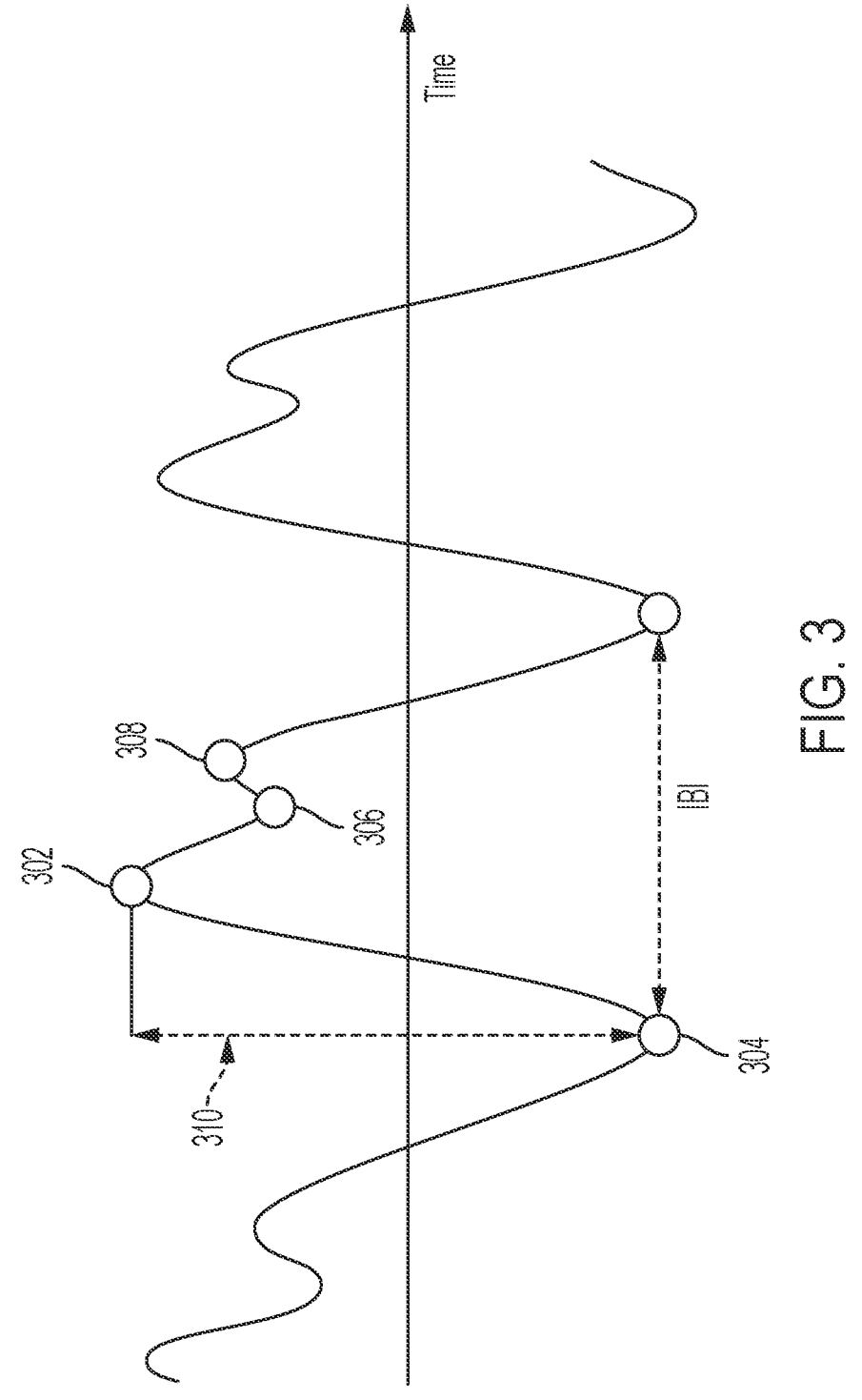
FIG. 3 shows an ideal AC component of a PPG signal, under an embodiment.

FIG. 3 shows a blown up view of an ideal AC component. FIG. 3 shows a systolic point 302, i.e. the beginning point of heart muscle contraction which pumps blood out of the heart. FIG. 3 shows a diastolic point 304, i.e. the end of a heart muscle contraction when chambers begin to refill again. The dicrotic notch 306 describes the point at which the aortic valve closes. A second wave point 308 of the signal corresponds to reflected pressures attributed to closing of the aortic valve. The anacrotic phase comprises the rising edge of the pulse shown in FIG. 3. The catacrotic phase comprises a falling edge of the pulse. Vasoconstriction 310 (as illustrated in FIG. 3) comprises an indication of pulsatile changes in blood volume. FIG. 3 also illustrates an interbeat interval (IBI).

As already stated, the PI is very small when the light emitter and photo-detector are placed on human skin. Values on a human wrist can vary from 0.05% to potentially 10% or more if the emitter and detector are placed directly on an artery. When the light emitter and photo-detector are placed on animal fur, the PI is more erratic and even smaller. This is due to the fact that animal fur impedes a light path between detection device and skin and introduces an air gap between device and skin. When motion is introduced, the changes in the optical path, especially in the presence of an air gap, distorts the reflected signal.

A collar device is described herein to track the PI of animals at elevated activity levels. The collar device penetrates the fur to place or extend a light source and light detector closer to the animal's skin. The collar device also compresses the fur in a consistent manner regardless of activity to remove the introduction of an air gap and to decrease motion artifacts. Consistent skin contact and consistent fur compression also allows for accurate measurement of animal skin temperature. Skin temperature data allows real time assessment of animal health condition especially in regards to hypothermia and heat exhaustion.

Red (645 nm) or green (530 nm) light sources are typically chosen for PPG measurements. Red can penetrate 10 times deeper into the skin than green light, however the reflected light is much smaller. The shallower penetration of the green light makes it ideal for a motion-prone PPG system. According the light emitter emits green light, under one embodiment.

Figure 4:
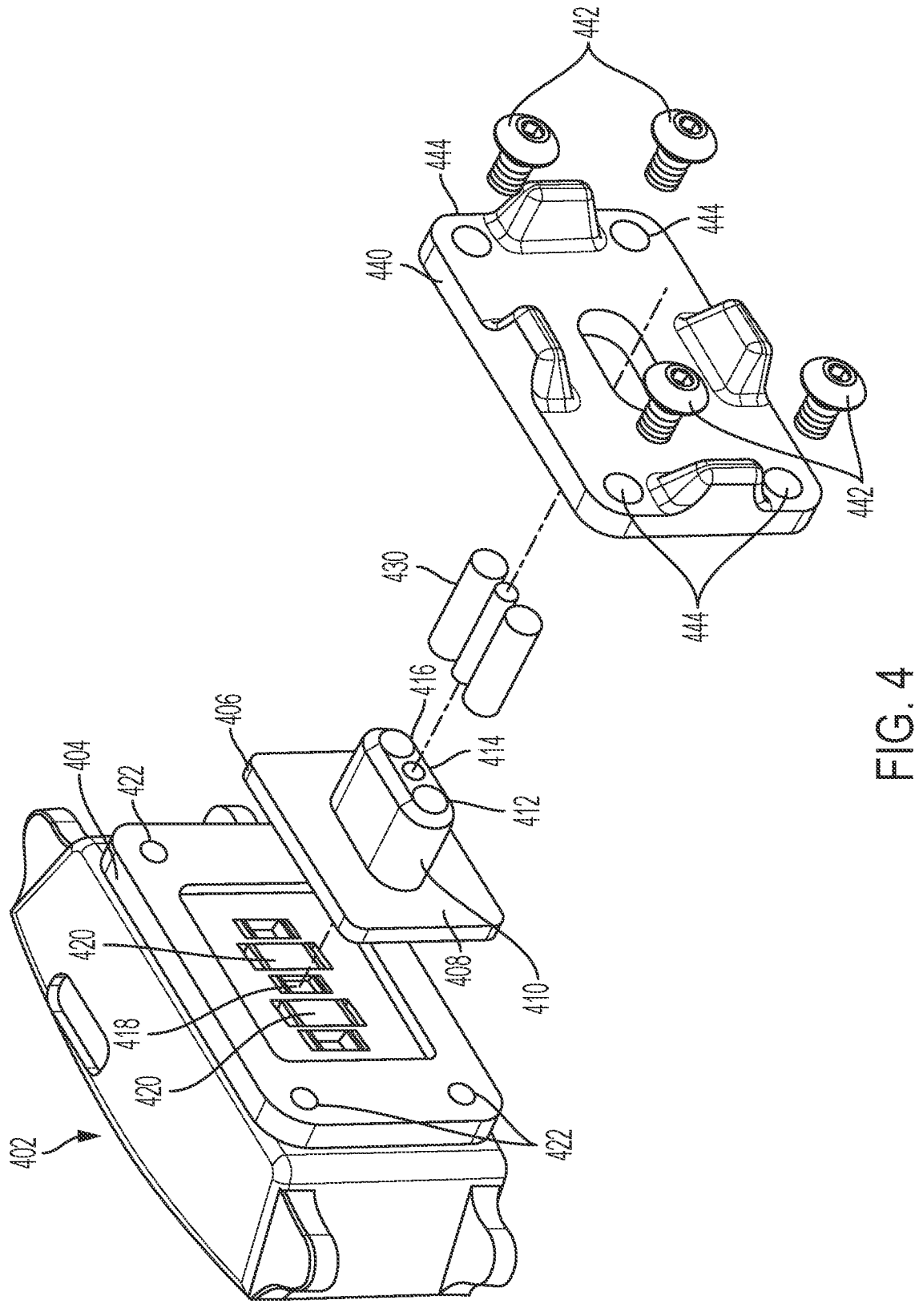
FIG. 4 shows a collar device, under an embodiment.

FIG. 4 shows a collar device. The device includes a collar component (or housing) 402 and a spacer component 406. The housing includes a base 404. The spacer component 406 includes spacer plate 408 and spacer protrusion 410 (also simply referred to herein as the spacer). The spacer 410 itself features three optical pathways 412, 414, 416. The collar component comprises a light emitter 418 and light detectors 420 The collar component also includes four screw bosses 422.

FIG. 4 shows a securement plate 440 for securing the spacer component 406 to the base 404 and housing 402. Screws pass 442 through receiving holes 444 of the securement plate 440 and are threadably received by the screw bosses 422. In such configuration, the spacer 410 (comprising the optical pathways 412, 414, 416) extends through an opening in the securement plate 440 as seen in FIG. 2.

Figure 5:
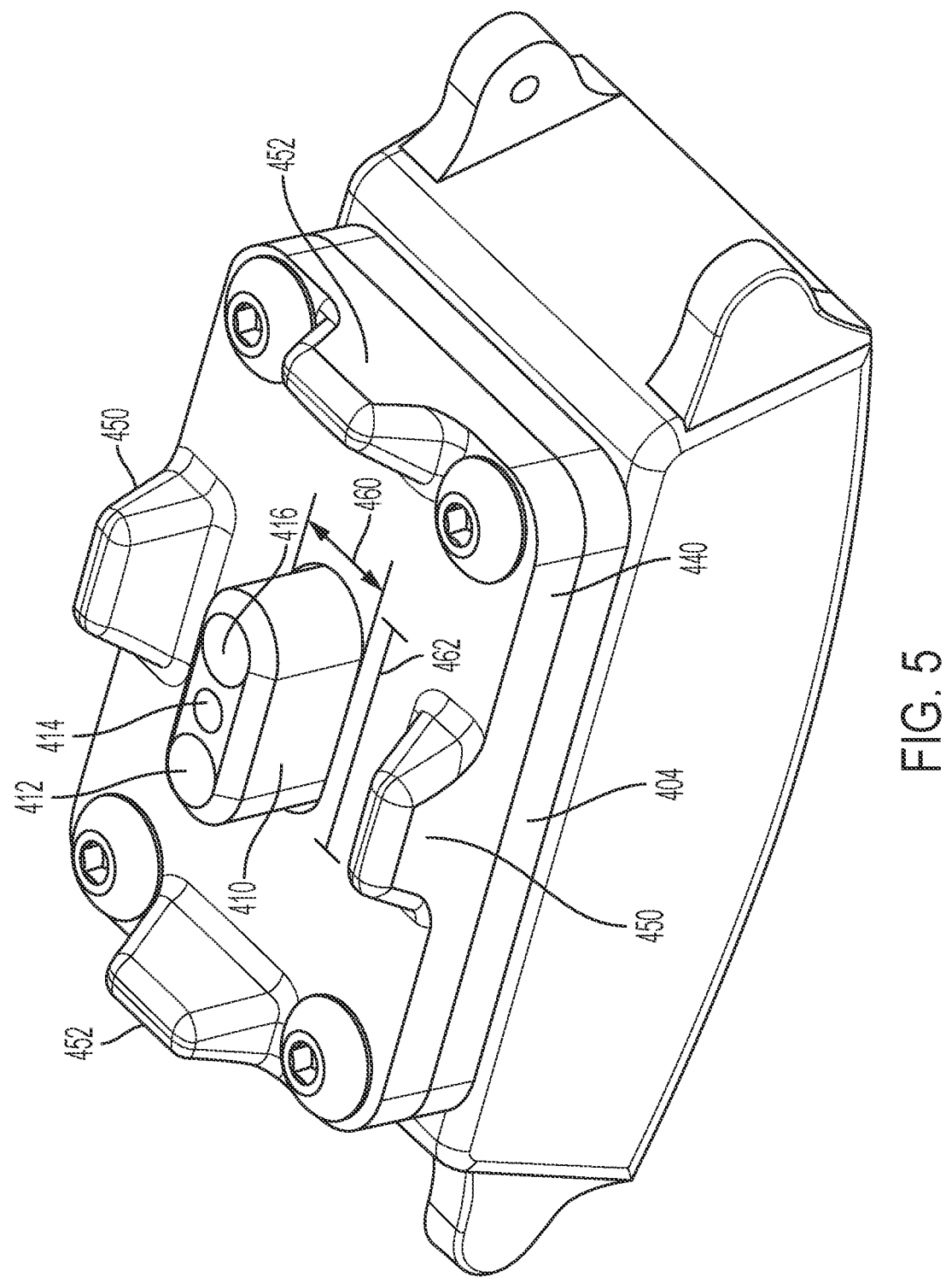
FIG. 5 shows a collar device, under an embodiment.

In a secured state, the translucent media 430 reside within the optical pathways, and the spacer plate 408 is seated directly atop the light emitter 418 and light detectors 420. (Light emitter and detectors are integrated into a circuit board residing in the housing.) The light emitter and detectors are positioned within a shallow rectangular recess of base 404. A peripheral rim of the rectangular recess receives and secures in place the spacer plate 408. The spacer plate 408 then locates optical pathway 412 and optical pathway 416 over light detectors 420, The spacer plate 408 also locates optical pathway 414 over the light emitter 418. FIG. 5 shows the spacer 410 (comprising the optical pathways 412, 414, 416) in a secured state.

As seen in FIGS. 4 and 5, the spacer 410 is mechanically secured to the main body of the collar device. In the secured state (and when worn by an animal as described herein), the spacer 410 creates a tension force between the wearable device and skin surface of the device wearer. The optical pathways 412, 416 provide a light path for detectors 420 on the device. The optical pathway 414 provides a light path for emitter 418. The optical pathways 412, 414, 416 comprise transparent or translucent media 430. The spacer pathways may be filled with a transparent or translucent material that stops 1-2 mm short of the skin contact point. The gap provides optical isolation of the emitter and detectors from surface reflections. The spacer itself may comprise a low gloss material with minimal reflective properties. These reflections (caused by reflective surfaces) may interfere with both the emission and detection of light. A raised barrier may be present between the emitter and detectors at the contact point with the skin/fur to keep surface reflections from bleeding from the emitter into a detector. The raised barrier acts as a gasket between the spacer and the skin. The air gap itself is not an issue, rather a varying of the air gap is what causes artificial fluctuations in the detector. Additionally, the raised barrier blocks incoming light. Like the air gap, fluctuations in the amount of ambient light causes variation in the values from the detectors.

Under an alternative embodiment, a first light emitter projects light through pathway 412 and a second light emitter projects light through pathway 416. A light detector then detects reflected light through pathway 414. Under such embodiment, light emitters are positioned at locations 420 while a light detector is positioned at location 418. Additional embodiments may include any configuration of projection/detection pathways.

Under one embodiment, the pathways comprise open air channels. Under such embodiment, the reflection pathway must comprise a highly polished surface in order to reflect light. If the translucent material is a self-contained internal light reflection material such as fiber optic then the spacer wall reflectivity is irrelevant.

A light pipe is a self-contained channel of light where light travels much like water through a garden hose. When the medium of the light is an open air channel, the body of the channeled surface becomes a shell of the light pipe. Hence, reflection of light is required. It's beneficial for the channeled surface to be finished in such a way that the light will be reflected and refracted away from the emitter or toward the detector, relative to their respective role. A straightforward way to accomplish this is to polish the channeled wall surface.

Figure 6:
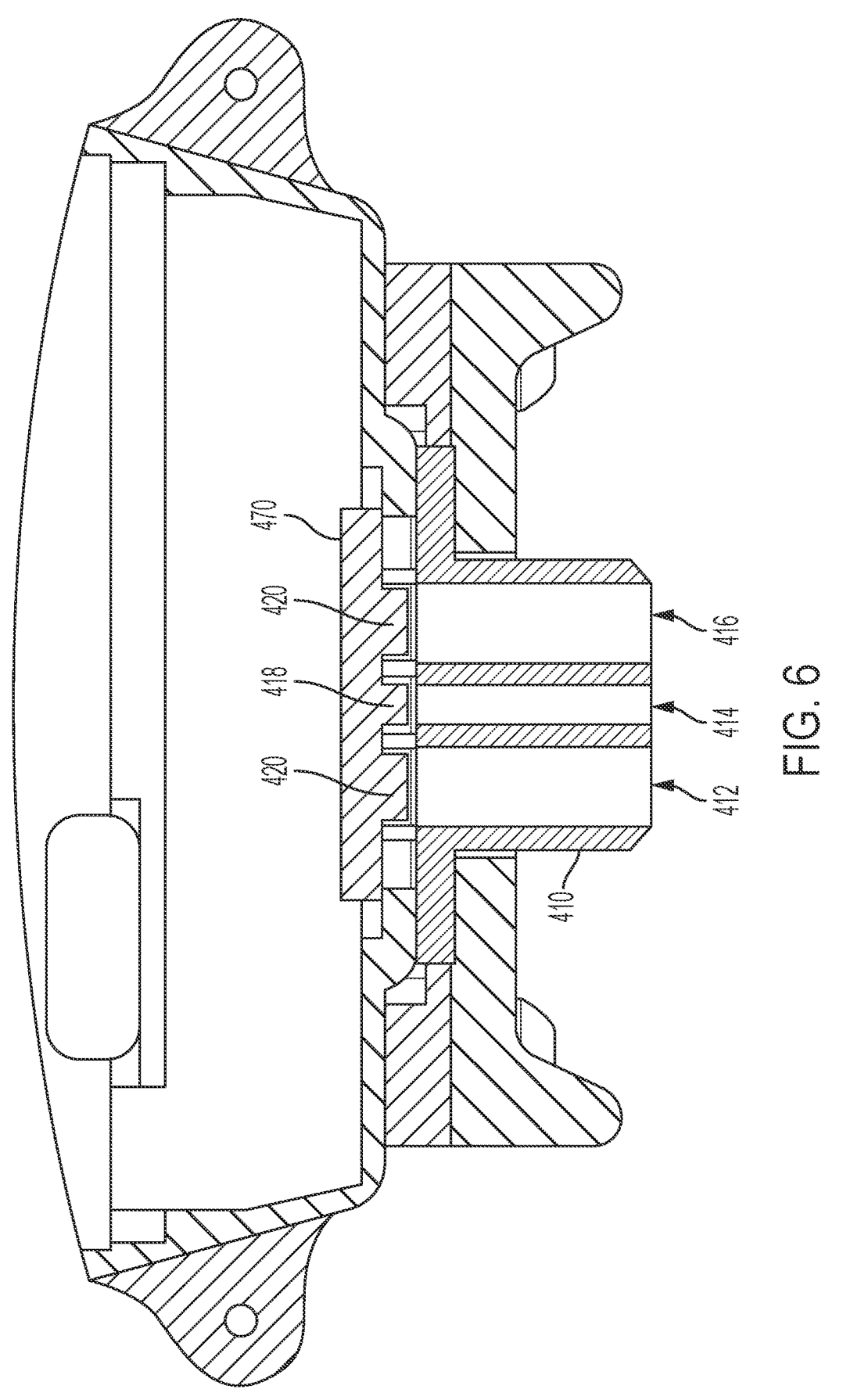
FIG. 6 shows a cross sectional view of a collar device, under an embodiment.

FIG. 6 shows a cross-sectional view of the collar device and spacer component, under an embodiment. FIG. 6 shows spacer 410 with optical pathways 412, 414, 416. FIG. 6 also illustrates a circuit board 470 positioning a light emitter 418 over optical pathway 414 and light detectors 420 over the optical pathways 412, 416.

Figure 7:
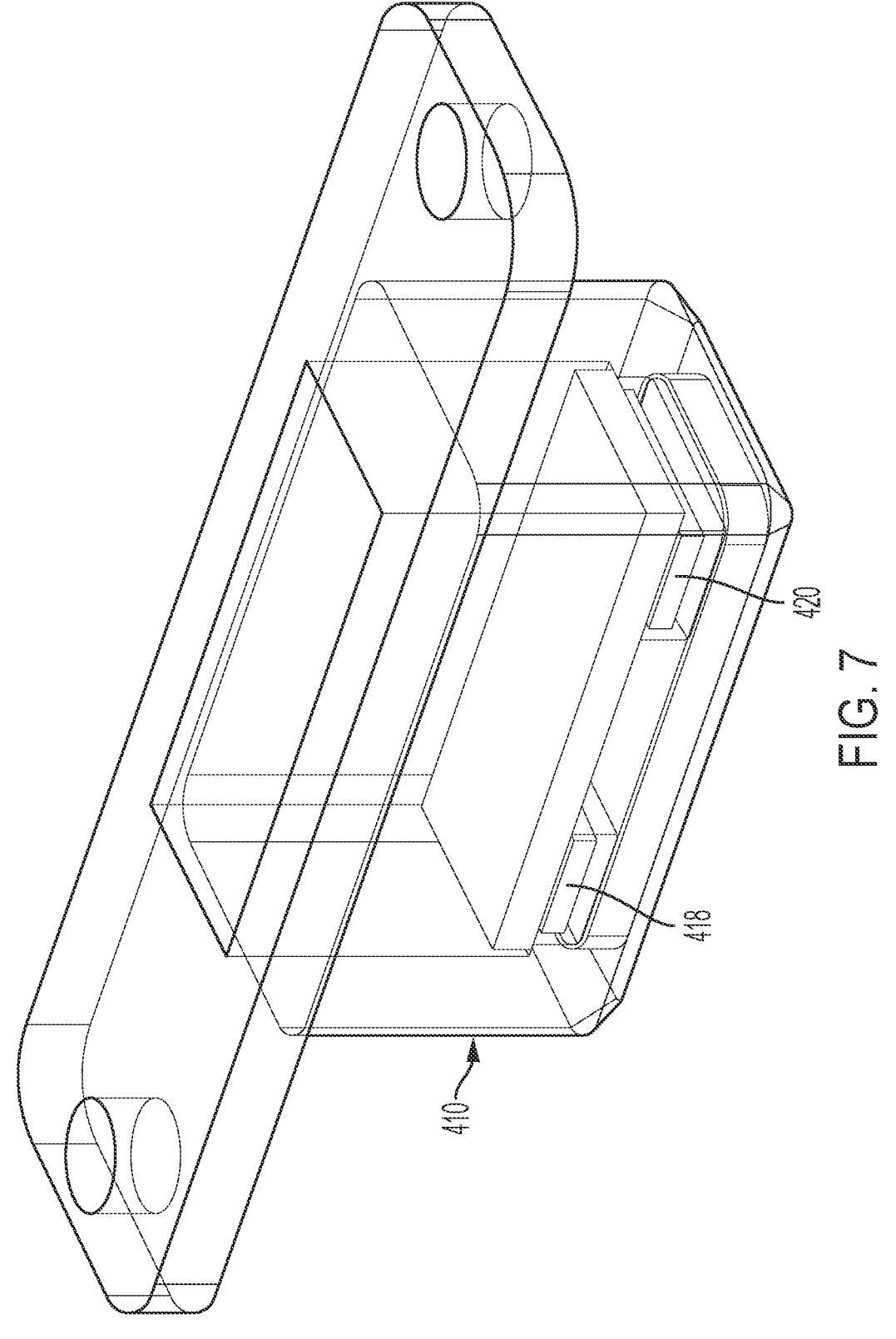
FIG. 7 shows a spacer component, under an embodiment.

Under an alternative embodiment shown in FIG. 7, a light emitter 418 and photo detector 420 are positioned at the end of the spacer 410 at the contact point with the skin/fur. The light emitter and photodetector may reside on a printed circuit board assembly (PCBA) 490 which is configured to direct operation of emitter/photodetector. The PCBA may also be electrically connected or coupled to circuity within the housing. This embodiment allows for the previously discussed spacer advantages while minimizing optical loss through any optical transfer material. This approach compacts and displaces fur, allowing for more direct skin contact, the same as previous embodiments. Since the emitter and detector are at the tip of the spacer, there is no need to add any optical coupling material, minimizing any loss that this feature may induce. An optical barrier is under an embodiment positioned between the emitter and detector to prevent the detection of direct-path light from the emitter. The goal is to detect the return scatter of light from within the skin and minimize any direct light from the emitter being detected.

As seen in FIGS. 4 and 5, the spacer component 406 including spacer 410 is removably attached to the housing of the collar. Therefore, it may be removed for cleaning. The spacer component may also be replaced with longer or shorter spacers (or different spacer configurations) based on fur and skin properties of the particular breed. Under another embodiment, the spacer component is not removable.

Figure 8:
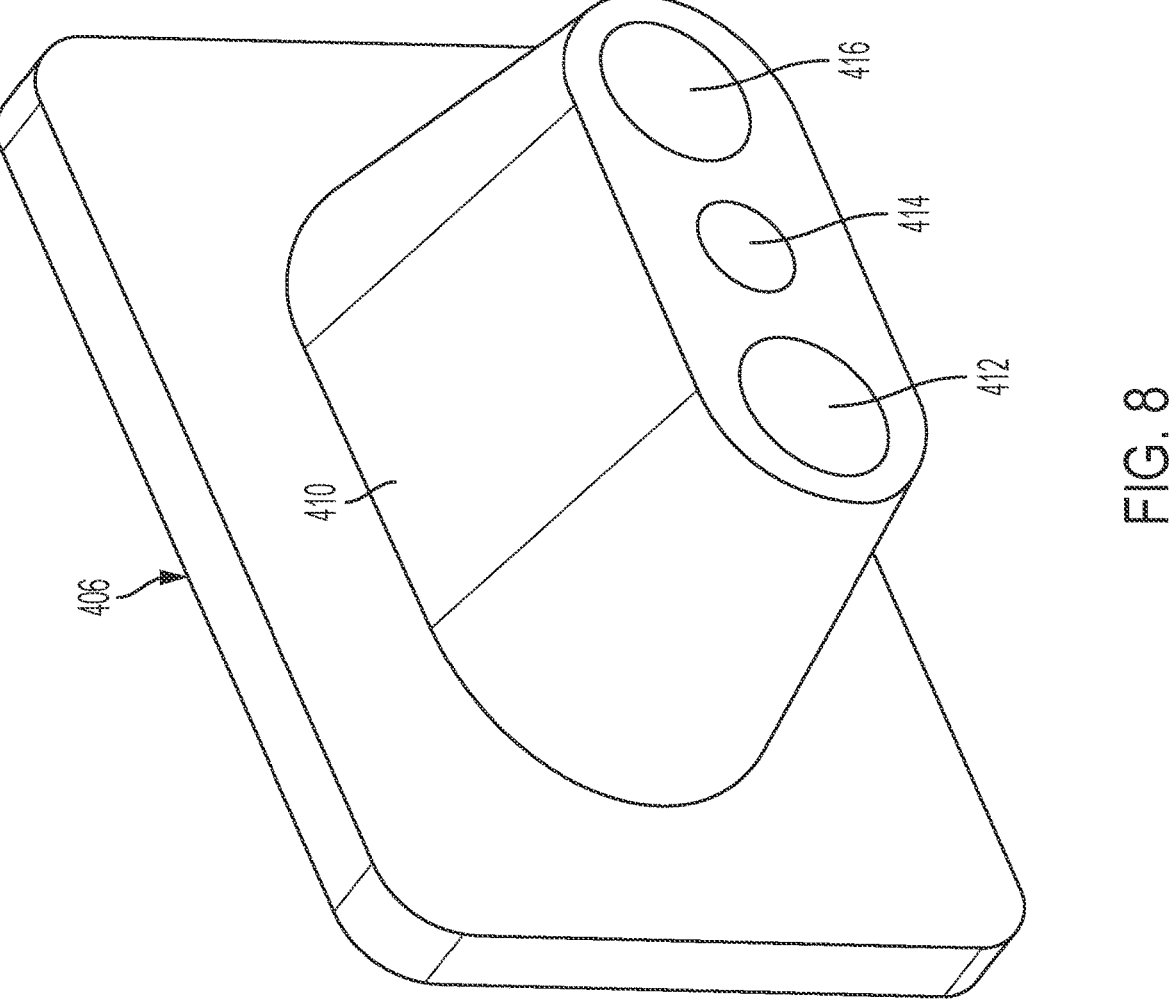
FIG. 8 shows a tapered configuration of a spacer, under an embodiment.

When the collar device is worn by the animal, the spacer 410 is directed towards the fur and skin of the animal. When the spacer 410 approaches the fur, some of it is directed away from the device by the spacer itself. The spacer comprises a protrusion with a constant width 460 and a length 462 at proximal and distal ends. Under one embodiment, the spacer 410 is tapered, i.e. the spacer diminishes in width and/or length from proximal end to distal end. FIG. 8 shows a tapered configuration of the spacer 410. The taper diverts fur in either direction of the spacer and reduces the contact surface area of the distal end. What fur that is not diverted is then compressed between the distal end of the spacer and the skin.

Figure 9:
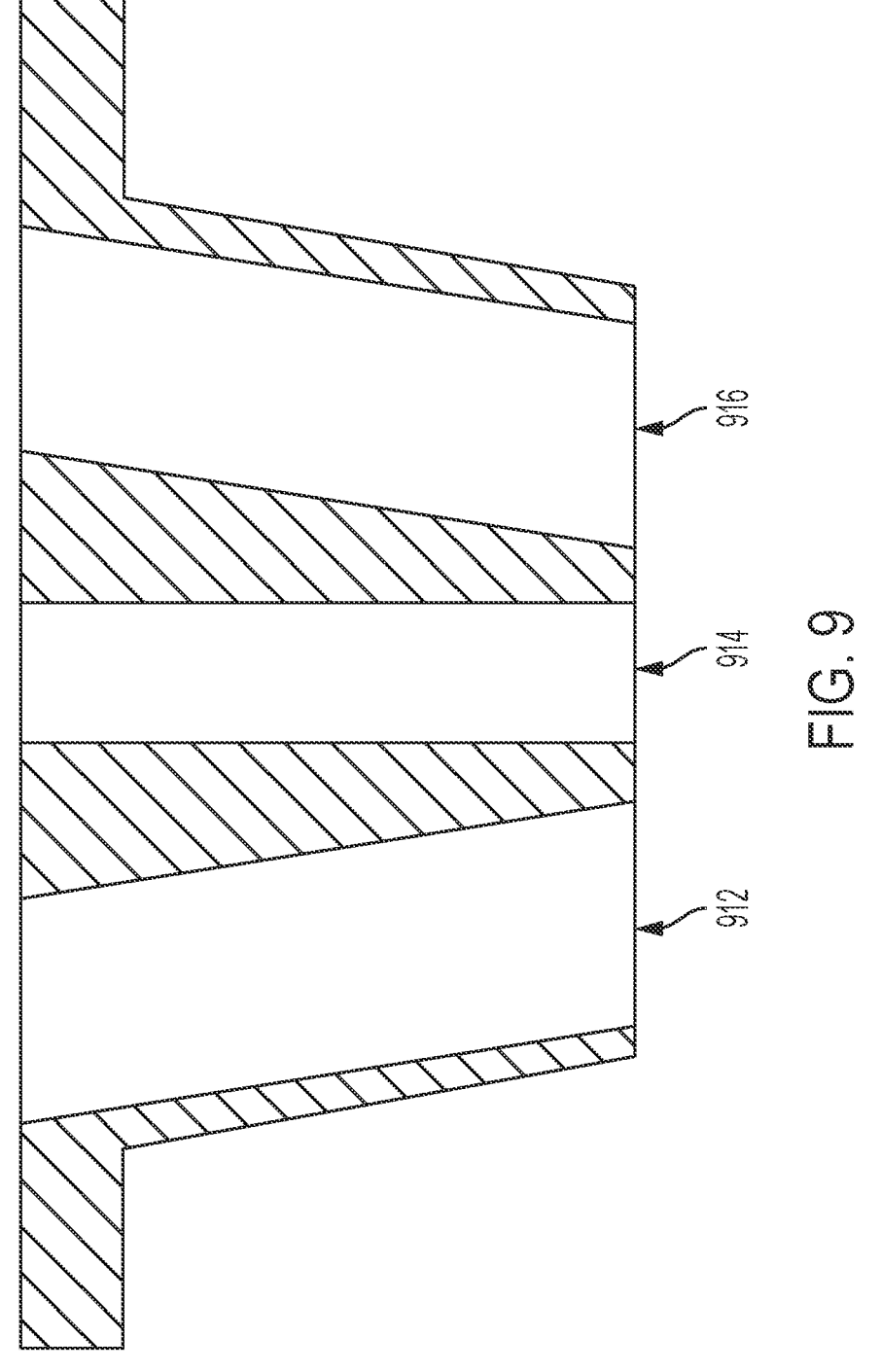
FIG. 9 shows a nonparallel optical pathways of a spacer, under an embodiment.

As seen in FIGS. 4 and 5, the spacer pathways 412, 414, 416 are parallel. Under an alternative embodiment, a spacer 410 may include a light path geometry comprising nonparallel pathways. FIG. 9 shows nonparallel pathways 912, 914, 916. Typically, the distance between the photodiode and the LED is adjusted so that optimal performance is reached. The spacer embodiment of FIGS. 4 and 5 may therefore be shortened or lengthened. However, this adjustment can be achieved by the use of non-parallel light guides.

FIG. 5 shows anti-tilt standoff spacers (or support feet) 450, 452 on the bottom of the device. Standoff spacers 450 are positioned laterally on opposing sides of the spacer and are laterally aligned with the spacer. Standoff spacers 452 are positioned on longitudinally opposing sides of the spacer and are longitudinally aligned with the spacer. Each spacer comprises a protrusion extending toward skin of the animal when the collar device is worn. Each spacer extends from a peripheral edge of securing plate 440. An outer surface of each protrusion is parallel with a peripheral surface of the securing plate 440. An inner surface of each protrusion tapers from its proximal end to its distal end. The anti-tilt standoff spacers prevent the tilting and twisting of the collar device which may lift the light emitter and detector off of the skin causing poor results. The addition of the anti-tilt spacers keeps the distal end of the spacer 410 flush against the skin. This limits reception by the detector of non-sensor driven light.

Under an embodiment, the device functions without the anti-tilt spacers described above. In addition, the spacer itself can shift and replace one of the support footers. The loading of the system is still balanced and the spacer itself is flush against the skin.

Although it is not necessary to remove all of the fur between device and skin, the presence of such fur reduces the intensity of the light. Hence the least amount of obstruction the better the signal. Therefore, it is important to reduce the variation of the air gap between the device and the skin. When worn by an animal, the device presses the distal end of the spacer towards skin and fur thereby maintaining a consistent layer of fur between spacer and skin. This positioning of the spacer results in contact between spacer and skin with more consistent optical properties.

As indicated above, the spacer comprises optical pathways 412, 414, 416. Under an embodiment, a light emitter emits light through at least one pathway and a detector detects reflected light through at least one pathway. The pathways may be filled with a translucent material, e.g. a clear epoxy. Under an alternative embodiment, a fiber optic filament may direct light to the skin along one pathway and from skin to the detector along another pathway. Under this embodiment, a body of the spacer may be produced from materials with reflective properties.

The spacer described above in FIGS. 4 and 5 comprises a relatively simple light path. However, the use of fiber optics enables more complicated pathways. For example a curved pathway is possible. Accordingly two pathways may diverge away from each other along their respective pathways from skin to a circuit board 470 in the housing. As a result, the emitter and detector may be further apart. This method gives flexibility to the circuit board layout and hardware design.

The collar device and spacer concept described above may also be used for temperature sensing. With spacer compressed against the skin of the animal, i.e. diverting fur as described above, the collar may send infrared light through one of the optical pathways to sense temperature. The spacer may also be used to house a thermal sensor.

Under one embodiment, the spacer comprises a thermally inert material (like rubber). One of the pathways may comprises a thermally conductive insert (like aluminum) to conduct heat from the animal's skin surface to a sensor on or coupled to the circuit board hardware. Temperature may be measured by a thermistor, temperature sensing integrated processor, or other direct measuring method. As an alternative, the entire spacer is made from thermally conductive material.

FIGS. 10-16 show embodiments of a spacer and temperature sensor.

Figures 10A, 10B:
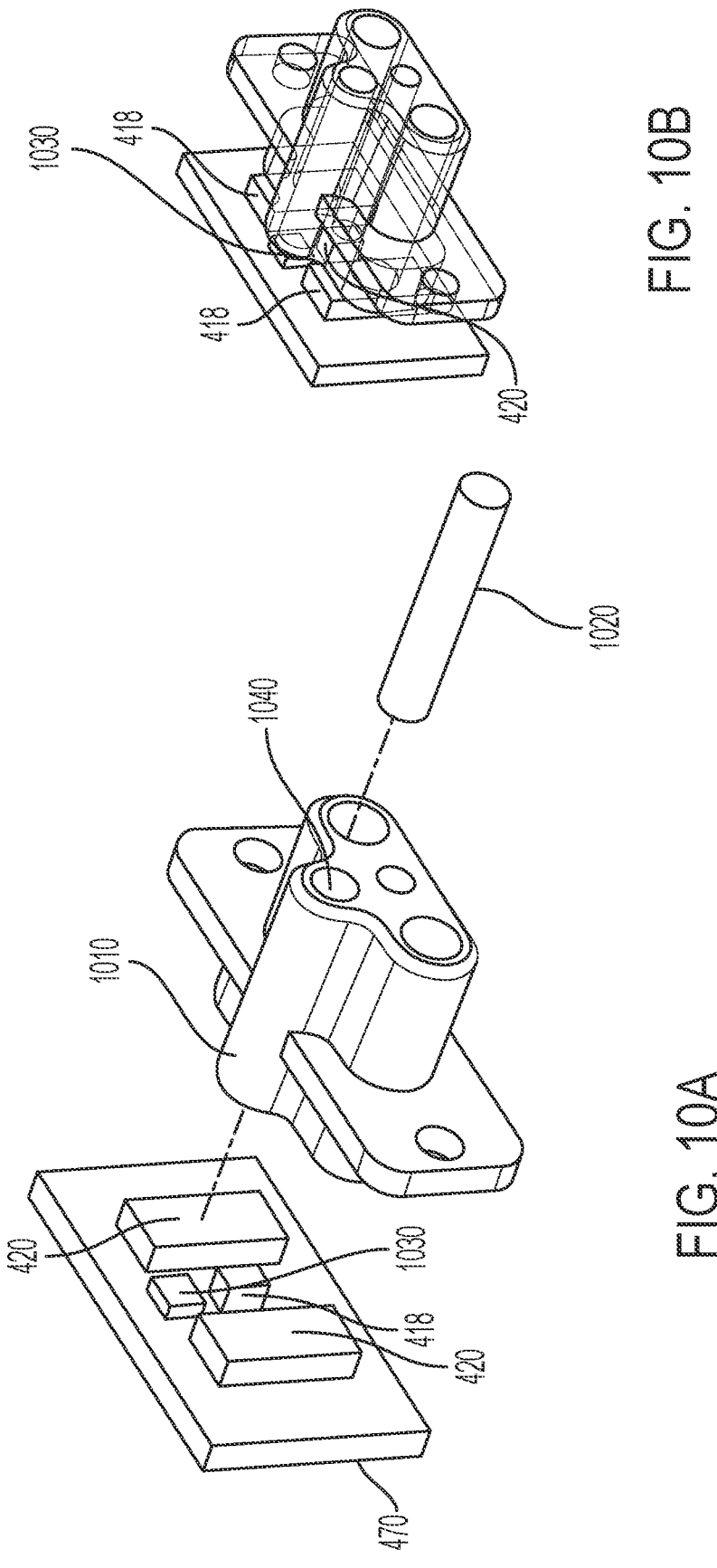
FIG. 10A shows a spacer and temperature sensor, under an embodiment.
FIG. 10B shows a spacer and temperature sensor, under an embodiment.

FIG. 10A shows a non-thermal conductive optical spacer 1010 (plastic, rubber, etc.). Pathway 1040 receives thermal conductive probe 1020 (aluminum, steel, etc.). In a secured state (see FIG. 10B), a proximal end of the thermal conductive probe 1020 contacts an I2C temperature sensor 1030. FIGS. 10-13 show light emitter 418 and light detectors 420 positioned on a circuit board 470 comprising one or more processors for controlling emitter/detectors.

Figures 11A, 11B:
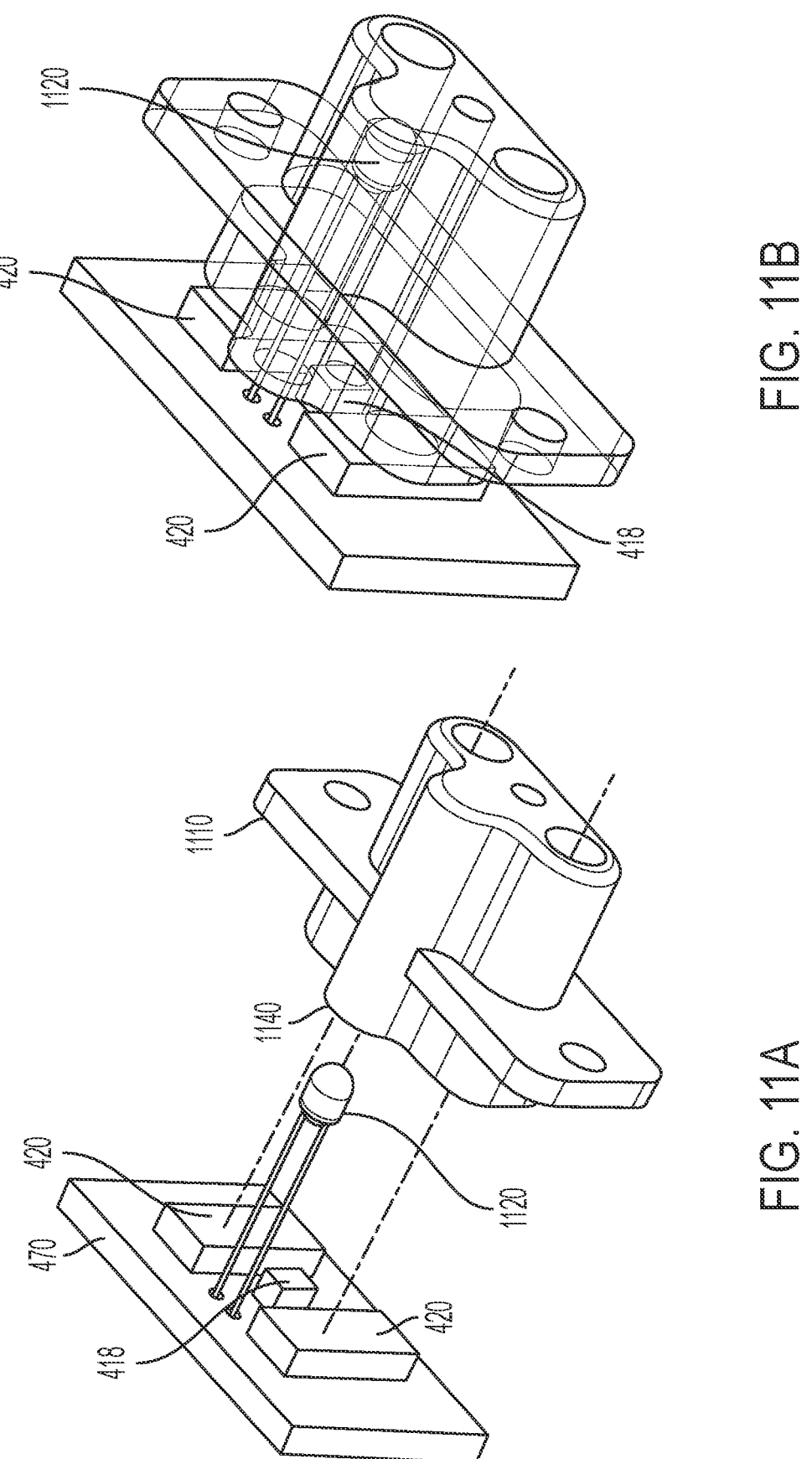
FIG. 11A shows a spacer and temperature sensor, under an embodiment.
FIG. 11B shows a spacer and temperature sensor, under an embodiment.

FIG. 11A shows a thermal conductive spacer 1110 (aluminum, steel, etc.). Pathway 1140 receives a thermistor temperature sensor 1120. In a secured state (see FIG. 11B), sensor 1120 resides completely within pathway 1140. Note that pathway 1140 has no opening at its distal end. Sensor 1120 is surrounded by and detects heat conducted by the thermal conductive spacer 1110.

Figure 12A:
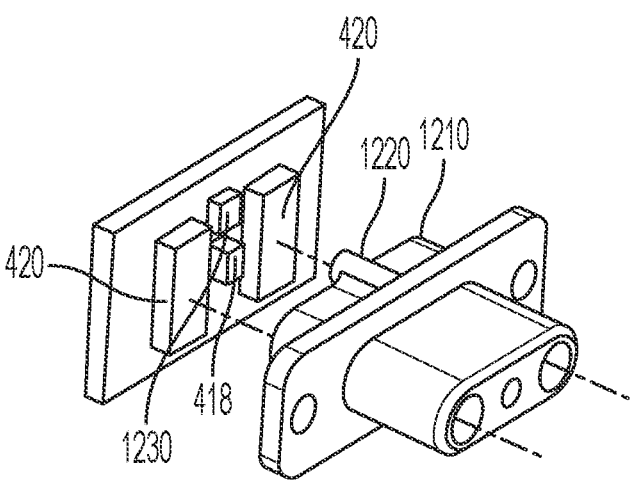
FIG. 12A shows a spacer and temperature sensor, under an embodiment.
Figure 12B:
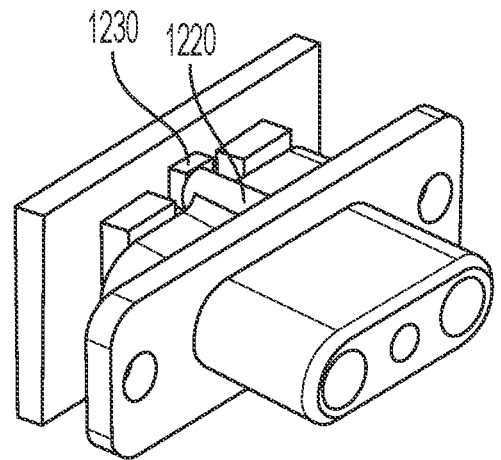
FIG. 12B shows a spacer and temperature sensor, under an embodiment.
Figure 12C:
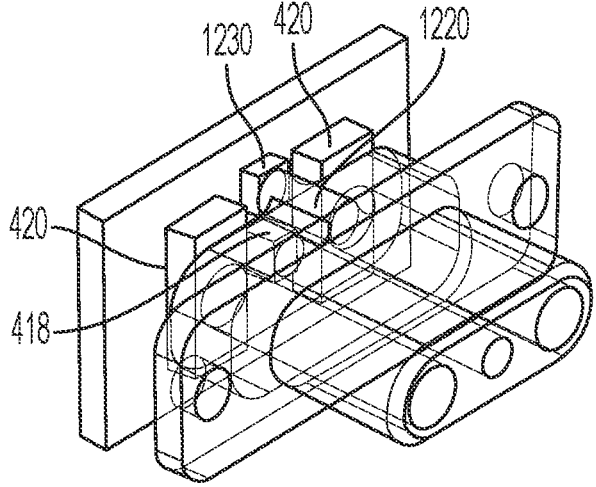
FIG. 12C shows a spacer and temperature sensor, under an embodiment.

FIG. 12A shows a thermal conductive spacer 1210 (aluminum, steel, etc.). A contact probe 1220 is seated in the conductive spacer 1210. Under an embodiment, the contact probe is integrally formed with the spacer. In a secured state (see FIGS. 12B and 12C), probe 1220 contacts an I2C temperature sensor 1230.

Figures 13A, 13B:
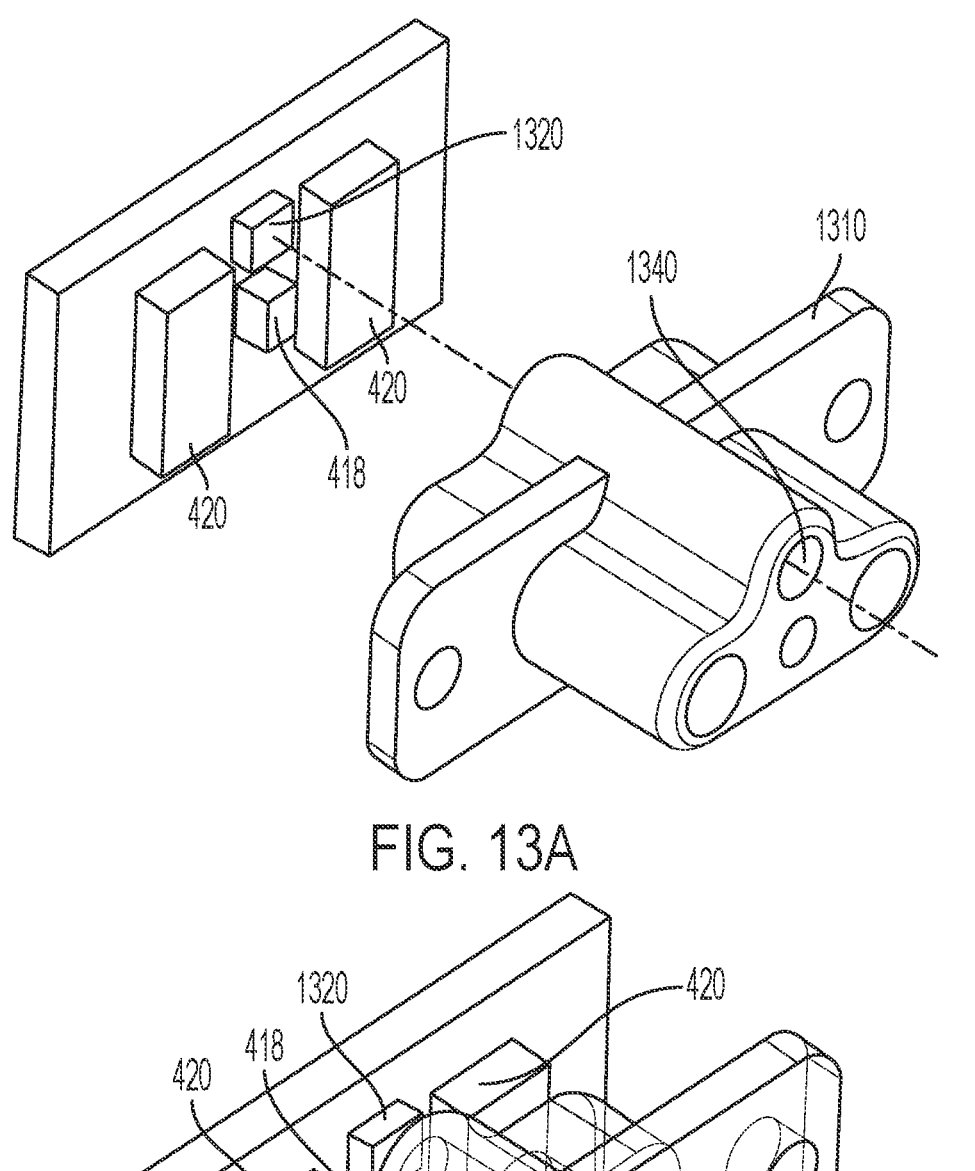
FIG. 13A shows a spacer and temperature sensor, under an embodiment.
FIG. 13B shows a spacer and temperature sensor, under an embodiment.

FIGS. 13A and 13B show an optical spacer 1310 with an open air channel 1340. FIG. 13A shows an IR temperature sensor 1320. In a secured state, an IR temperature sensor 1320 may send infrared light through open air channel 1340 to sense temperature.

Figures 14A, 14B, 14C:
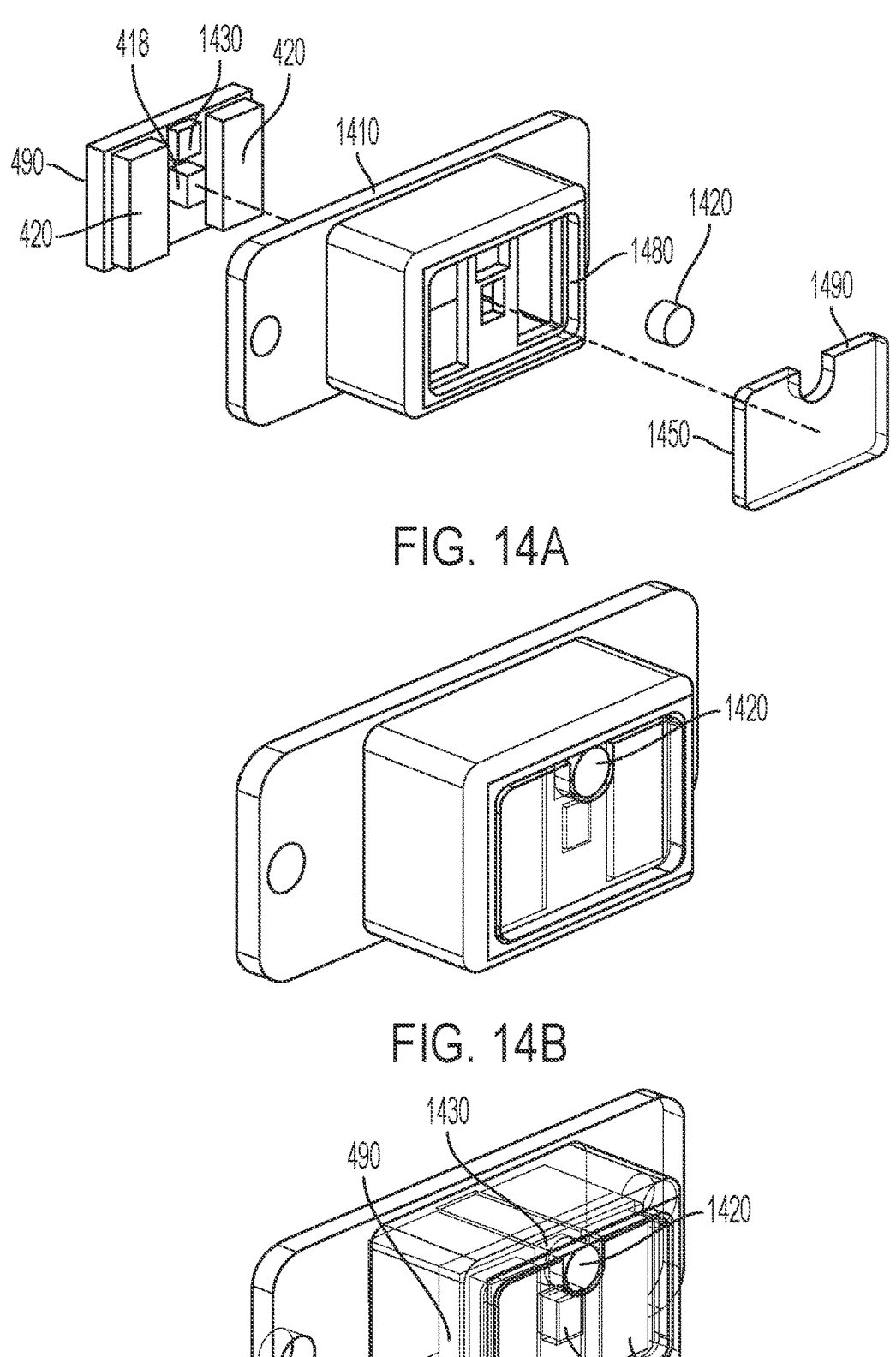
FIG. 14A shows a spacer and temperature sensor, under an embodiment.
FIG. 14B shows a spacer and temperature sensor, under an embodiment.
FIG. 14C shows a spacer and temperature sensor, under an embodiment.

FIG. 14A shows a non-thermal conductive spacer 1410 (plastic, rubber, etc.). FIG. 14A shows an I2C temperature sensor 1430 and a thermal conductive probe 1420 (aluminum, steel, etc). A lens component 1450 comprises a U shaped recess for receiving and securing the thermal conductive probe 1420. A recess of the spacer comprising a peripheral wall 1480 is dimensioned to receive an outer peripheral wall 1490 of the lens component. In a secured state (see FIGS. 14B and 14C), the lens component secures and positions the probe in a contact position providing contact between the probe 1420 and sensor 1430. The lens is transparent. The main function of the lens is to allow transmission of light from the emitter and back to the photo diode while preventing debris and liquids from contacting/corrupting/damaging the emitter and photo diodes or otherwise entering the sealed interior of the device case. The placement of the emitter and detectors is analogous to the configuration shown in FIG. 7. In contrast to FIGS. 10-13, light emitter 418 and photo detectors 420 are positioned at the end of the spacer 410 at the contact point with the skin/fur. The light emitter and photodetector may reside on a printed circuit board assembly (PCBA) 490 which is configured to direct operation of emitter/photodetector. The PCBA may also be electrically connected or coupled to circuitry within the housing. FIGS. 15-16 illustrate similar positioning of the emitter/detectors.

Figure 15A:
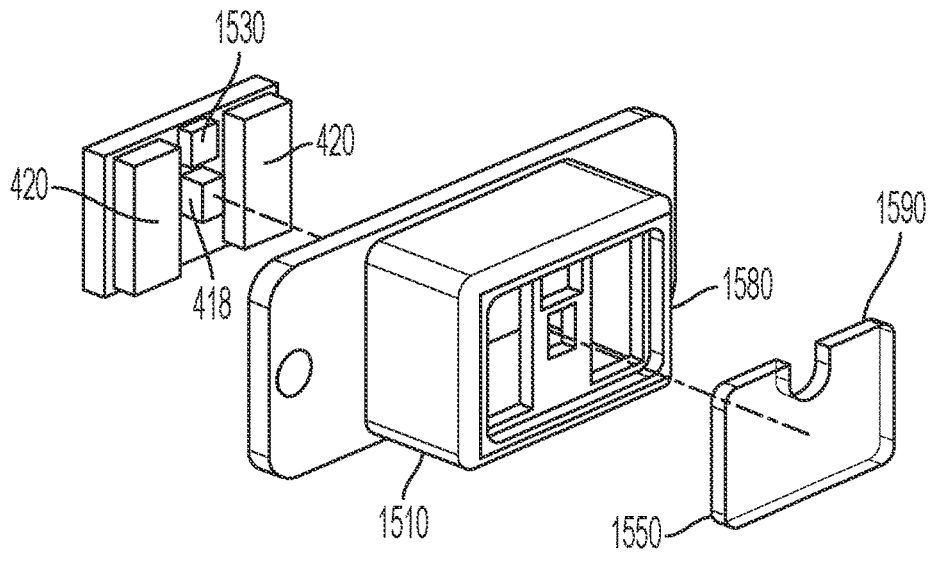
FIG. 15A shows a spacer and temperature sensor, under an embodiment.
Figure 15B:
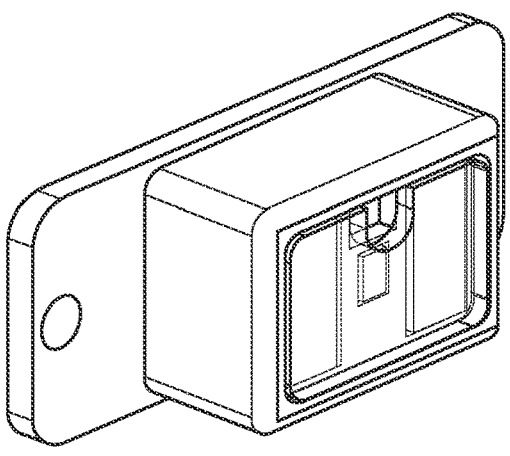
FIG. 15B shows a spacer and temperature sensor, under an embodiment.
Figure 15C:
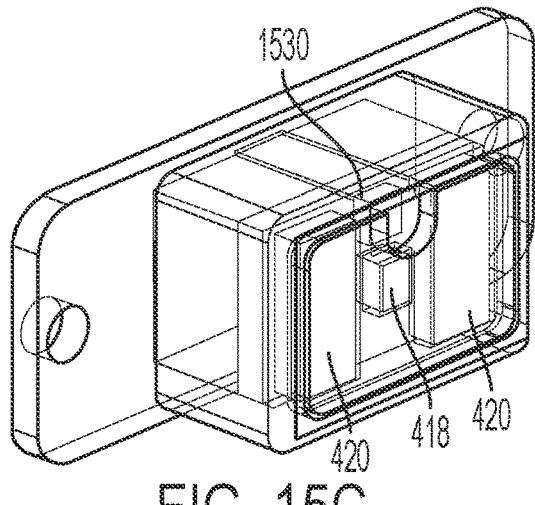
FIG. 15C shows a spacer and temperature sensor, under an embodiment.

FIG. 15A shows a non-thermal conductive spacer 1510 (plastic, rubber, etc.). FIG. 15A shows an IR temperature sensor 1530. FIG. 15A shows a lens component 1550. A recess of the spacer comprising a peripheral wall 1580 is dimensioned to receive an outer peripheral wall 1590 of the lens component. In a secured position (see FIGS. 15B and 15C), the lens component 1550 comprises a U shaped open passageway between the IR temperature sensor 1530 and skin of the animal. The lens is transparent. The main function of the lens is to allow transmission of light from the emitter and back to the photo diode while preventing debris and liquids from contacting/corrupting/damaging the emitter and photo diodes or otherwise entering the sealed interior of the device case.

Figure 16A:
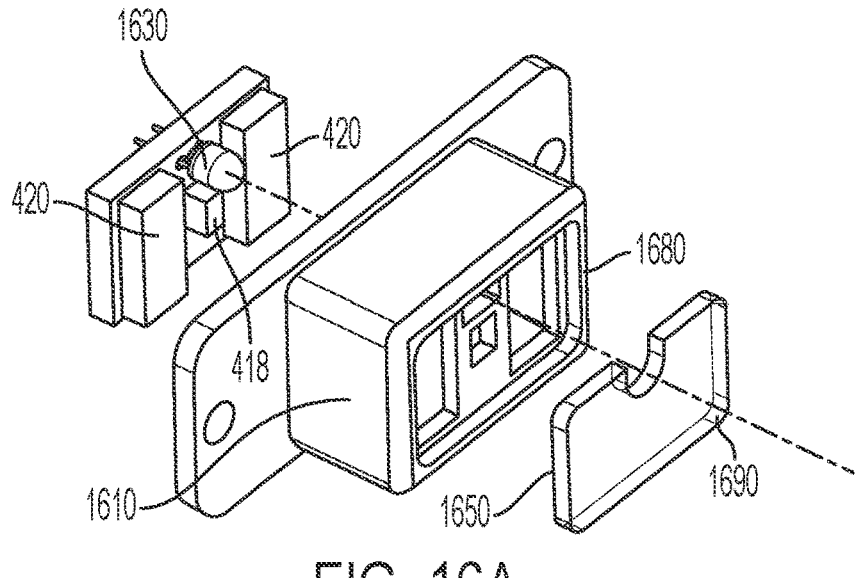
FIG. 16A shows a spacer and temperature sensor, under an embodiment.
Figure 16B:
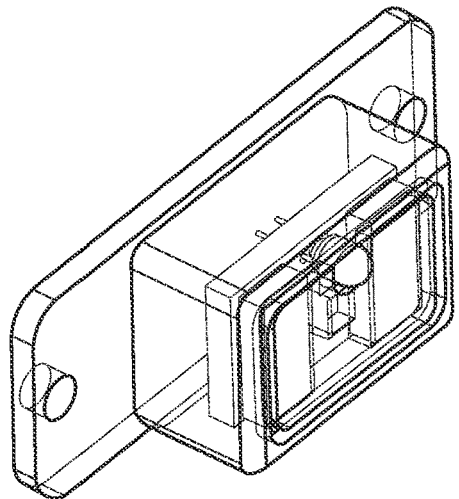
FIG. 16B shows a spacer and temperature sensor, under an embodiment.
Figure 16C:
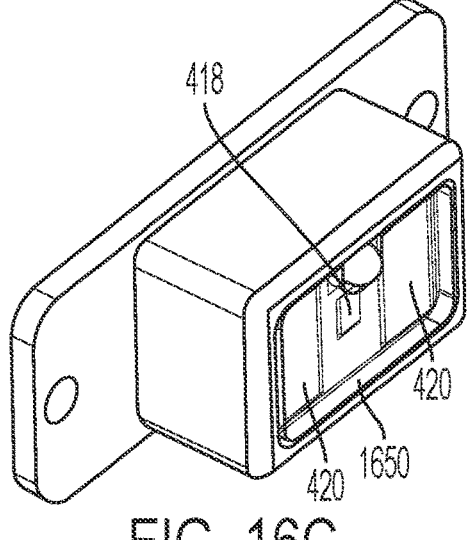
FIG. 16C shows a spacer and temperature sensor, under an embodiment.

FIG. 16A shows a non-thermal conductive spacer 1610 (plastic, rubber, etc.). FIG. 16A shows a thermistor temperature sensor 1630. FIG. 16A shows a lens component 1650. A recess of the spacer comprising a peripheral wall 1680 is dimensioned to receive an outer peripheral wall 1690 of the lens component. In a secured position (see FIGS. 16B and 16C), the lens component 1650 comprises a U shaped open passageway between the thermistor temperature sensor 1630 and skin of the animal. The lens is transparent. The main function of the lens is to allow transmission of light from the emitter and back to the photo diode while preventing debris and liquids from contacting/corrupting/damaging the emitter and photo diodes or otherwise entering the sealed interior of the device case.

Figure 17:
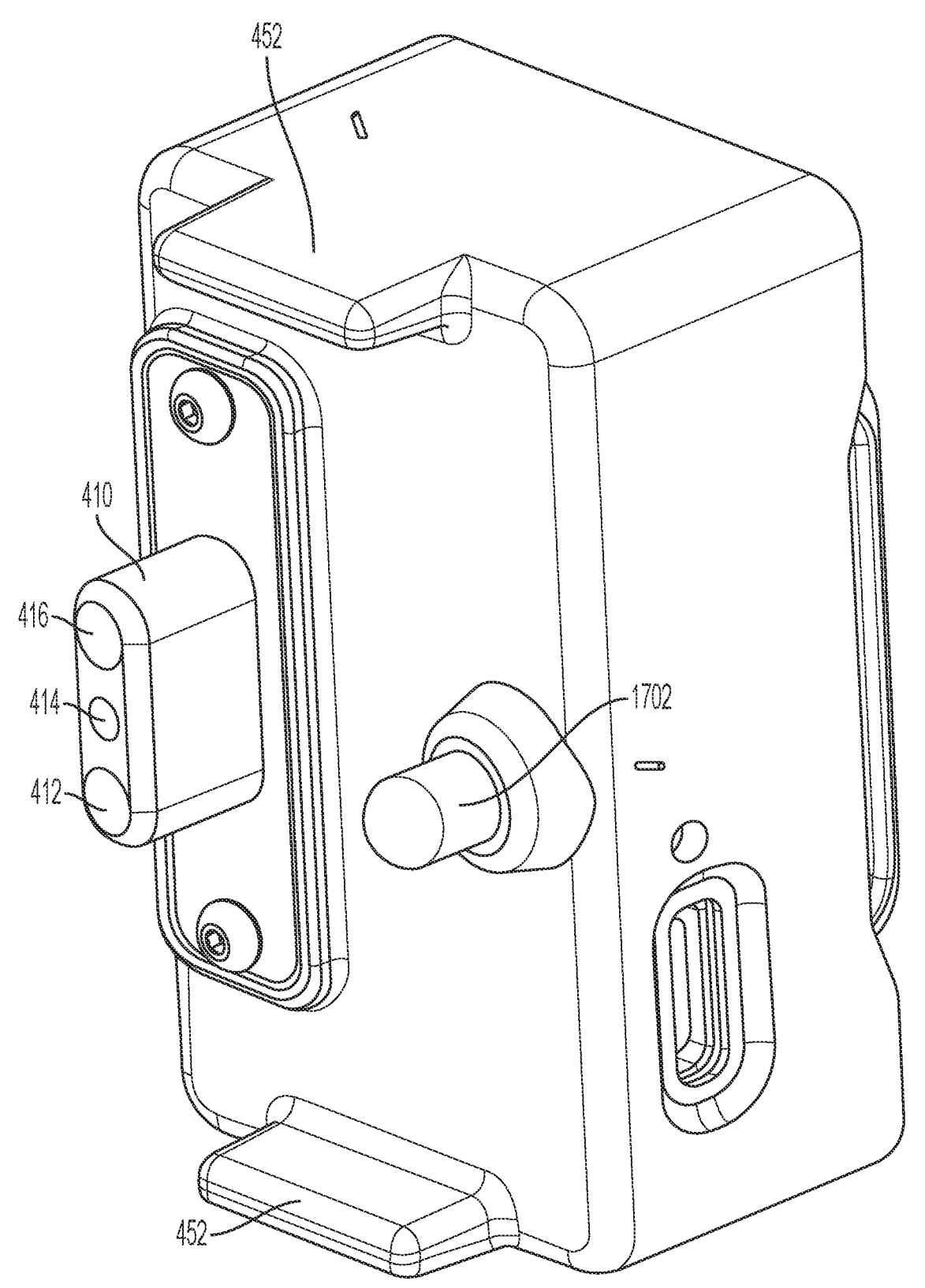
FIG. 17 shows a collar device, under an embodiment.

FIG. 17 shows an embodiment of a collar device which features a temperature probe 1702. FIG. 17 also features anti-tilt spacers 452 placed at longitudinally opposed peripheral edges of the device. FIG. 17 discloses a spacer 410 and temperature probe 1702 at longitudinally opposed peripheral edges of the device. The spacer 410 and probe 1702 replace the laterally placed anti-tilt spacers 450 of FIG. 5.

Figure 18:
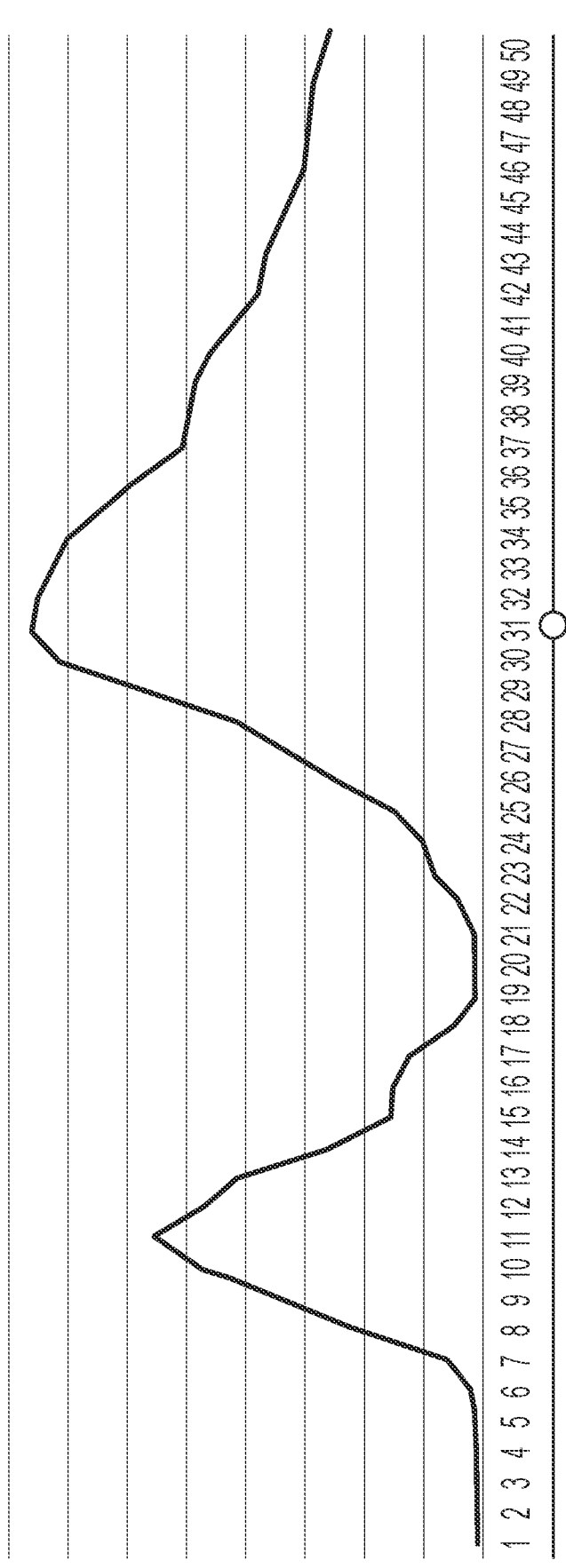
FIG. 18 shows a PPG signal of a motionless animal, under an embodiment.
Figure 19:
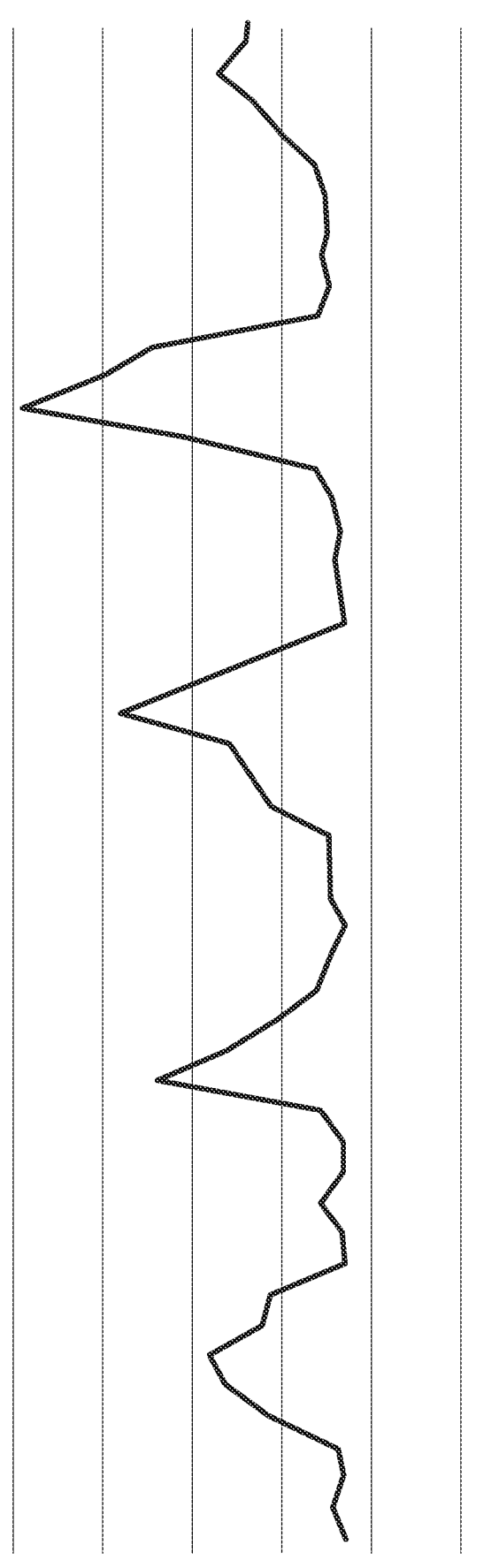
FIG. 19 shows a PPG signal of an animal in motion, under an embodiment.

FIGS. 18-19 show average heart rate values of an animal detected by the apparatus and methods of detecting the PPG signal in animals described above.

The process of heart rate determination typically follows the following sequence, either in real-time or as post-processed data, under an embodiment.

Turn the LED (as described above) OFF (note that the LED typically emits green light but embodiments are not so limited).

Read and store the voltage level of a photodetector (as described above) via an analog to digital converter (ADC). This stored value is a measure of the ambient light level.

Turn the LED on.

Read and store the voltage level of a photodetector via an ADC converter.

Turn the LED off.

Read and store the voltage level of a photodetector via an ADC converter. This stored value is a second measure of the ambient light level. Subtract the average of the two ambient light levels from the "LED ON" photodetector voltage level and store this value. This result represents the direct, reflected, and scattered light level picked up by the photodetector and may be referred to as "green count".

The steps above (ending in storing a green count value) are repeated at a rate fast enough to detect changes in blood pulsation and also any light path changes induced by motion of the subject. This rate is typically between 25 Hz and 400 Hz.

The green count values are stored in a "first-in-first-out" (FIFO) memory buffer. This memory buffer can hold anywhere from several seconds of green count data to several minutes of green count data; depending on the complexity of the heart-rate algorithm.

The green count stream is typically band-pass filtered to remove the DC and low frequency components due to non-pulsatile blood reflections and high frequency components due to movement.

Following the filtering, a peak-detect process is run. This peak detect process picks off the AC components in the green count stream. A peak can be defined as a higher point in a curve surrounded by lower points. A peak-detect algorithm utilized for PPG can look for polarity changes in the slope of the PPG trace. These AC components represent the pulsatile blood reflections and remaining noise components. The magnitude of the detected peak values are stored into a second FIFO. Under an embodiment, minimally complex algorithms may stop at this point and utilize the second FIFO data to analyze the systolic peak to systolic peak count versus time to determine a heart rate value.

Under other embodiments, more complex algorithms integrate signals from an accelerometer to attempt to remove AC components of the green count stream that were due to movement. A number of adaptive noise cancellation methods can be implemented. The result of this step is the PPG signal with motion artifacts removed. The digital representation is stored in a third FIFO memory buffer.

A frequency tracking algorithm utilizes the FIFO memory buffer to determine an averaged heart rate.

During each processing step, the components of the signal that are filtered out may also be stored and processed. The difference between the values filtered out and the values that remain are an indication of the optical signal quality, the optical signal quality being heavily influenced by optical coupling and movement. This difference value can be used as a "signal quality" or "heart rate confidence" indication. This value indicates a "believability" level of the heart rate value. With good optical coupling, the heart rate value will be more accurate and confidence level will be higher.

FIG. 18 shows a PPG signal of a motionless animal, under an embodiment. The figure illustrates 2-seconds of data captured at 25 samples per second.

FIG. 19 shows a PPG signal of an animal in motion, under an embodiment. The figure illustrates 2-seconds of data captured at 25 samples per second.

Figure 20:
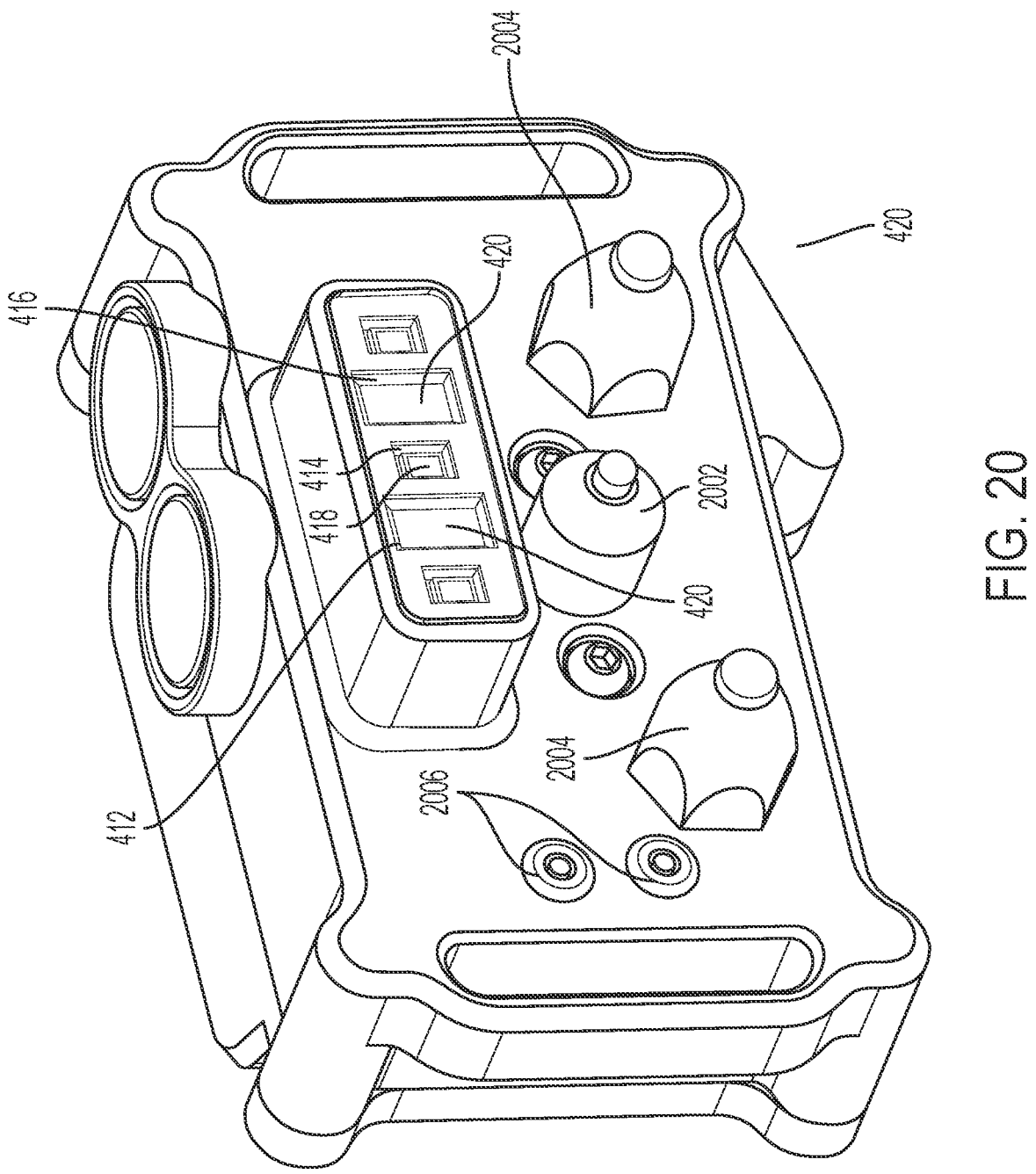
FIG. 20 shows a collar device, under an embodiment.
Figure 21:
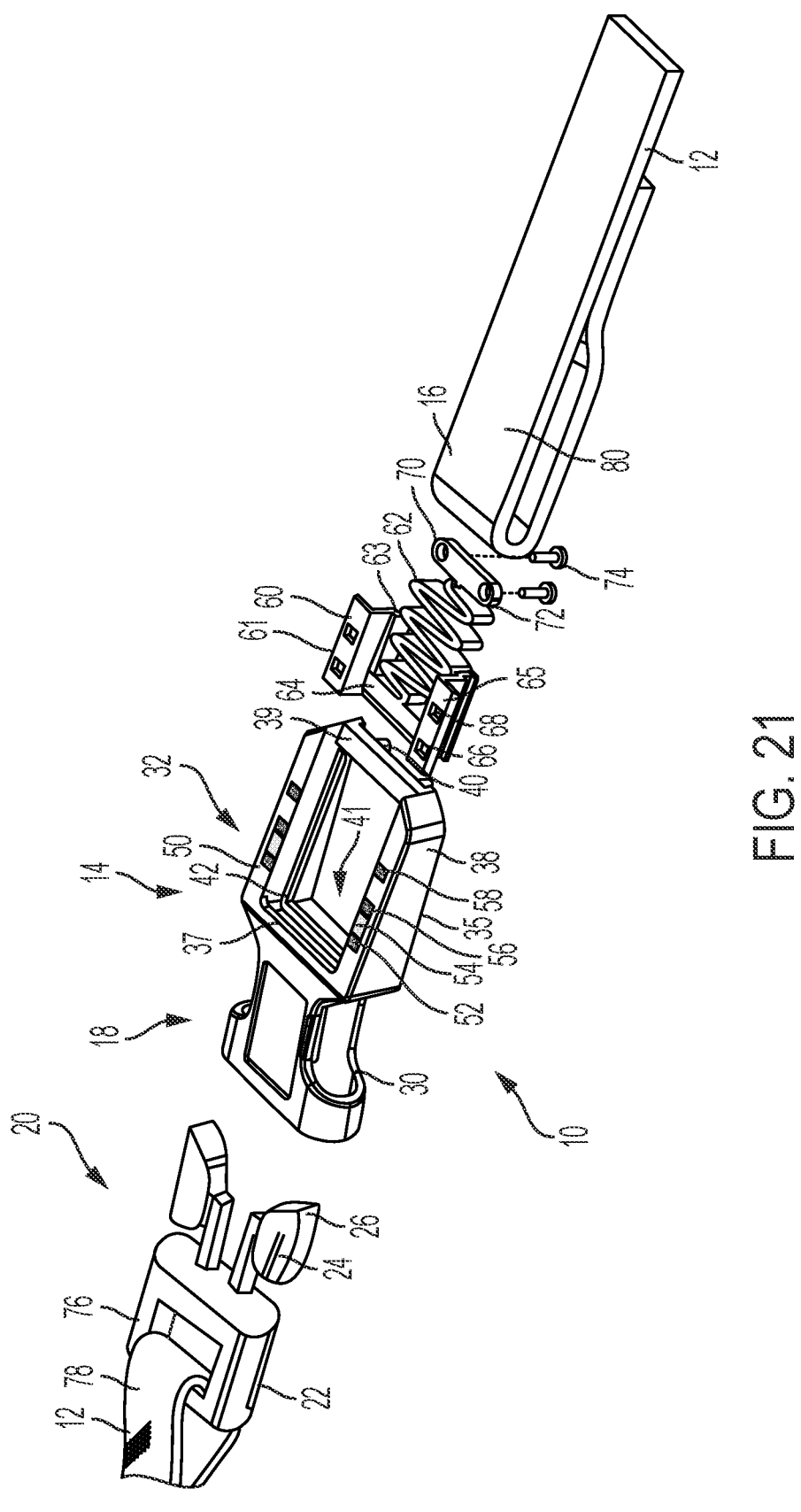
FIG. 21 is an exploded, perspective view of a pet collar, under an embodiment.

FIG. 20 shows another embodiment of a collar device for detecting and monitoring a PPG signal in animals. Using a spacer configuration analogous to the configurations shown in FIGS. 14-16, light emitter 418 and photo detectors 420 are positioned at the end of the spacer 410 at the contact point with the skin/fur. The light emitter and photodetector may reside on a printed circuit board assembly (PCBA) which is configured to direct operation of emitter/photodetector. The light emitter 418 resides above optical pathway 414 and the light detectors reside above optical pathways 412, 416. The PCBA may also be electrically connected or coupled to circuity within the housing. This collar device includes a skin temperature sensor 2002, under an embodiment. The housing includes circuitry for delivery of a negative stimulus through probes 2004. The housing also features water sensors 2006.

The collar device may be paired with a flexible compliance collar attachment to ensure snug fit throughout activity. This flexible compliance collar (i.e. a collar for securing a collar device to an animal) is described in detail below.

With reference FIGS. 21-25 there is a shown a pet collar 10, under an embodiment. The pet collar 10 is configured to be worn about the neck of a pet, such as a dog or cat, in conventional fashion. The collar 10 includes an elongated flexible strap 12 and a plastic buckle 14 coupled to opposite ends 16 of the strap 12.

The strap 12 may be made of any conventional material, such as a woven material, plastic, leather, or the like. The strap 12 may include a folded over portion which allows for generally adjusting of the length of the strap 12. The strap 12 may also include a conventional known, unshown D-ring to allow the collar 10 to be coupled to a leash.

The buckle 14 is a two piece, squeeze type release buckle having a first portion, receiving portion or receiver 18 and a second portion, clip portion, or clip 20. The clip 20 includes a coupling base 22 from which extends two resilient prongs 24. The two prongs 24 are designed to be flexed inwardly towards each other during the coupling process to create an outward spring force upon the prongs 24. Each prong 24 terminates at an enlarged latch 26.

The receiver 18 includes a strap coupling portion or catch portion 30 and a tension indicator portion 32. The catch portion 30 cooperates with the clip 20 for releasable engagement or coupling therebetween. The catch portion 30 has a central channel 34 configured to receive the clip prongs 24 therein. With the clip prongs 24 fully positioned within the central channel 34, the prong latches 26 are releasably positioned within two side channels or notches 36 extending laterally from the central channel 34.

The tension indicator portion 32 extends longitudinally from the catch portion 30. The tension indicator portion 32 has a base 35 having an end wall 37, two oppositely disposed side walls 38 and a front wall 39, which in combination define a shuttle opening or channel 41. The shuttle channel 41 has an internal peripheral guide rail, ridge, or tongue 42 extending inwardly from the end wall 37 and two side walls 38. Each side wall 38 has a top surface 50 having a series of position indicators, visual position indicators or tension indicator portions shown in the preferred embodiment as a first mark 52, a second mark 54, a third mark 56, and a fourth mark 58. The first mark 52, third mark 56, and fourth mark 58 have a first color coding, such as the color red, to indicate an improper tension or fit. The second mark 54 has a second color coding, such as green, to indicate a proper tension or fit. The first color is different from the second color so that they are readily discernable. The front wall 39 has two downwardly extending screw mounting bosses 40. The shuttle channel 41 is configured to slidably or movably receive a reciprocating tensioning member, slide or shuttle 60 therein.

The tensioning shuttle 60 includes two oppositely disposed side walls 61, an end wall 64 spanning the side walls 61, and a zig-zag or magazine compression spring 62 extending from the end wall 64 and at least partially positioned between the side walls 61. Each side wall 61 includes a guide channel or groove 63 configured to slidably receive the side wall guide tongue 42 of the base 35. Each side wall 61 also includes a laterally extending top flange 65 overlaying the base side walls 38. Each top flange 65 has a position indicator, visual tension indicator portion, or tension indicator in the form of a first viewing window 66 and a position indicator, visual tension indicator portion, or tension indicator in the form of a second viewing window 67 extending therethrough. The first viewing windows 66 may be aligned with the underlying first marks 52, second marks 54, or third marks 56, depending upon the longitudinal position of the tensioning shuttle 60 relative to the tension indicator portion 32. Similarly, the second viewing windows 68 may be aligned with the underlying third marks 56 and fourth marks 58, depending upon the longitudinal position of the tensioning shuttle 60 relative to the tension indicator portion 32.

The compression spring 62 includes an end mounting plate 70 having two screw mounting holes 72 therethrough. The end mounting plate 70 is mounted to the bottom of the base front wall 39 by passing two mounting screws 74 through the mounting holes 72 of the end mounting plate 70 and threading them into the bosses 40 of the base front wall 39.

Figure 22:
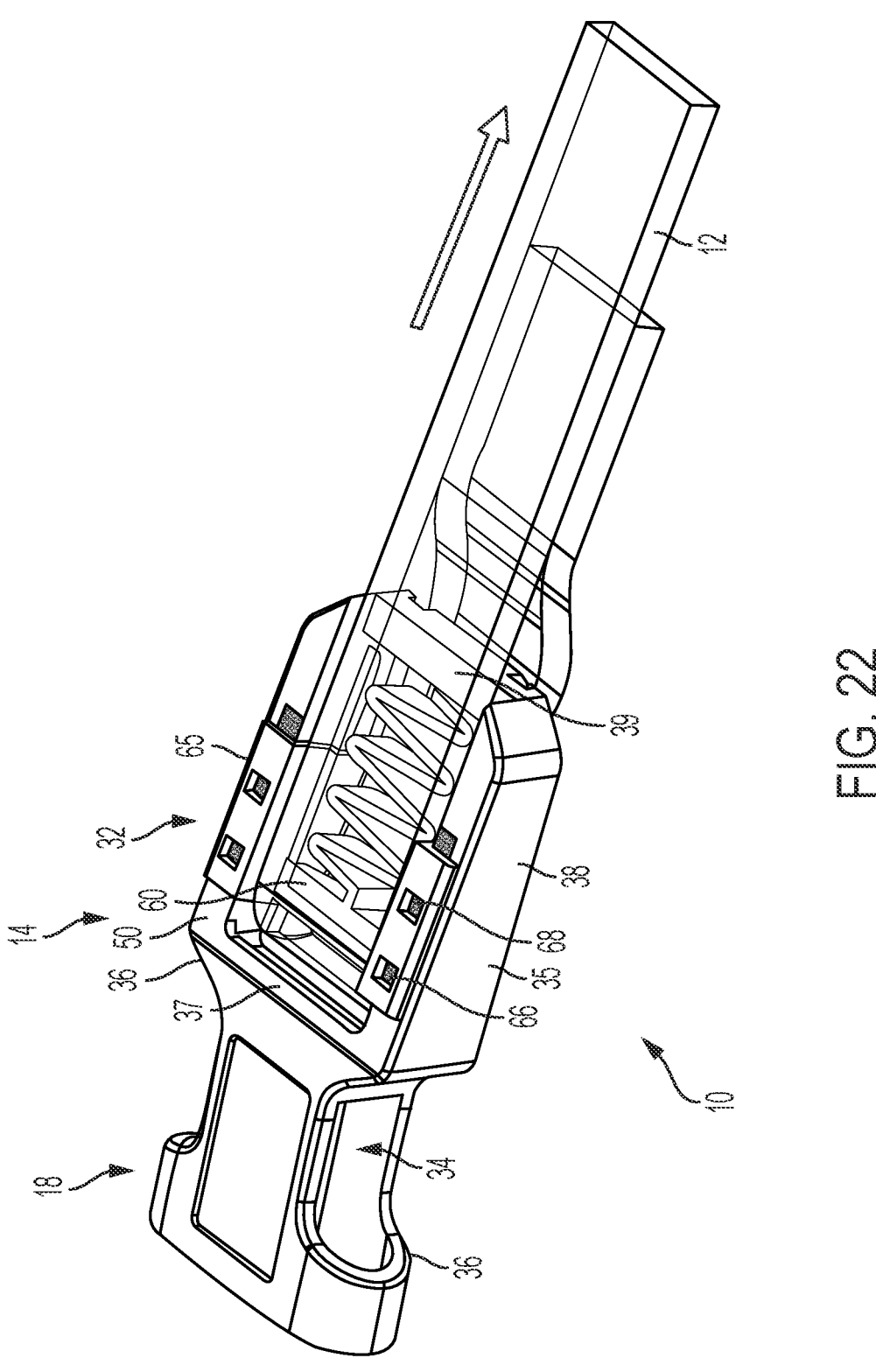
FIG. 22 is a perspective view of a buckle portion of a pet collar, under an embodiment.

A first end 78 of the strap 12 is coupled to the clip 20 through a strap opening 76 extending through the clip 20. A second end 80 of the strap, opposite first end 78, is coupled to the receiver 18 by wrapping the second end 80 about the tensioning shuttle 60, with the second end 80 passing through the shuttle channel 41 between the tensioning shuttle 60 and the base end wall 37, as best shown in FIG. 22. The compression spring 62 biases the tensioning shuttle 60 in a longitudinal direction away from the base front wall 39 and the strap second end 80 (except for the small portion at the strap second end bite or turn) coupled to the receiver 18.

In use, a pet owner attempts to select a proper length of the strap 12 in conventional fashion by adjusting the doubled over portion of the strap 12, or by any other conventionally known manner The collar 10 is then wrapped about the pet's neck and the buckle 12 is fastened by coupling the clip 20 to the receiver 18. With the clip 20 residing within the central channel 34 of the receiver 18, the prongs 24 are outwardly biased so that their latches 26 are nested within the side notches 36 to maintain the position of the clip 20 within the receiver 18. The clip 20 may be released from the receiver 18 by manually pushing or biasing the prong latches 26 inwardly and out of the side notches 36, whereby the clip 20 may then be extracted from the receiver central channel 34.

Figure 23:
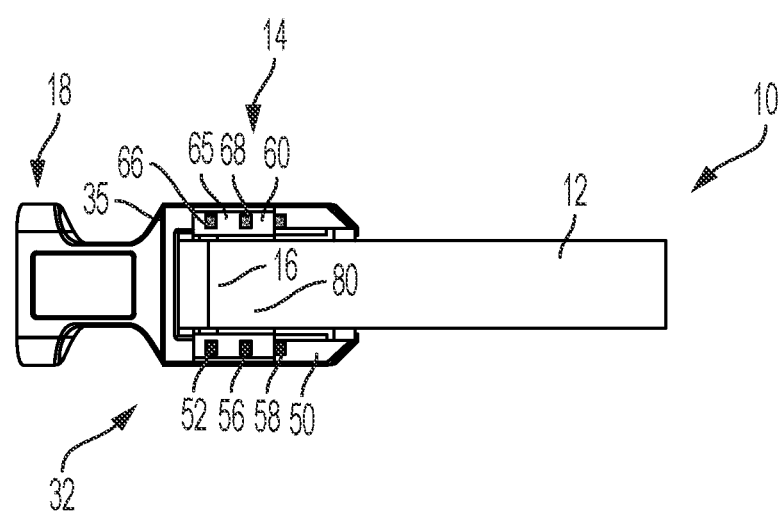
FIG. 23 is a top view of a buckle portion of a pet collar, under an embodiment.

As shown in FIG. 23, if the pet owner has mistakenly adjusted the length of the strap 12 to be too long or loose upon the pet, the first viewing window 66 is aligned with the first mark 52 and the second viewing window 68 is aligned with the third mark 56. With the color coding of red on the first and third marks 52 and 56 showing or viewable through the first and second viewing windows 66 and 68, and the exposure of the fourth mark 58 outside the position of the tensioning shuttle 60, the pet owner may immediately see that the tension/length of the strap 12 is too short or small and the collar is improperly loose. The pet owner may then remove the collar 10 and shorten the length of the strap 12 to gain a proper fit which is snugger upon the pet. This indication may also appear due to the diameter of the pet's neck decreasing over time after the initial sizing of the collar 10.

Figure 25:
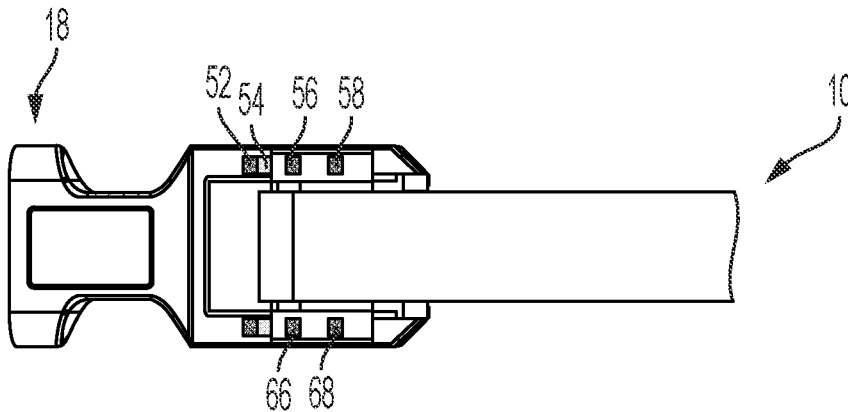
FIG. 25 is a top view of a buckle portion of a pet collar, under an embodiment.

As shown in FIG. 25, if the pet owner has mistakenly adjusted the length of the strap 12 to be too short or tight upon the pet, the first viewing window 66 is aligned with the third mark 56 and the second viewing window 68 is aligned with the fourth mark 58. With the color coding of red on the third and fourth marks 56 and 58 showing or viewable through the first and second viewing windows 66 and 68, and the exposure of the first mark 52 inside the position of the tensioning shuttle 60, the pet owner may immediately see that the tension/length of the strap 12 is too long or large and the collar is improperly tight. The pet owner may then remove the collar 10 and extend the length of the strap 12 to gain a proper fit which is looser upon the pet. This indication may also appear due to the diameter of the pet's neck increasing over time after the initial sizing of the collar 10.

Figure 24:
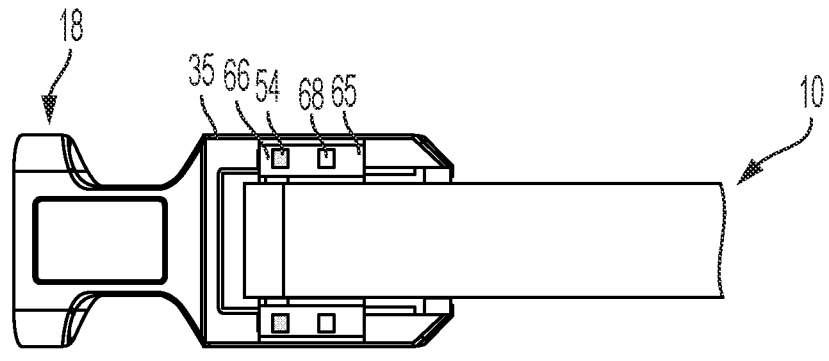
FIG. 24 is a top view of a buckle portion of a pet collar, under an embodiment.

As shown in FIG. 24, if the pet owner has correctly adjusted the length of the strap 12, the first viewing window 66 is aligned with the second mark 54 and the second viewing window 68 is aligned in the blank space between the third and fourth marks 56 and 58. Alternatively, another green mark may be place between the third and fourth marks 56 and 58 to provide a secondary green indicator through the second viewing window 68. With the color coding of green on the second marks 54 showing through the first viewing windows 66, the pet owner may immediately see that the tension/length is correct.

Thus, the first viewing window 66 is aligned with the second mark 54 when the tension from the flexible strap 12 upon the tensioning shuttle 60 is of a correct preselected amount which provides for a proper fit of the collar 10 upon a pet. The first viewing window 66 is aligned with the first mark 52 and the second viewing window 68 is aligned with the third mark 56 when the tension from the flexible strap 12 upon the tensioning shuttle 50 is of an amount less than the correct preselected amount for a proper fit upon the pet. The first viewing window 66 is aligned with the third mark 56 and the second viewing window 68 is aligned with the fourth mark 58 when the tension from the flexible strap 12 upon the tensioning shuttle 60 is of an amount greater than the correct preselected amount for a proper fit upon the pet.

Thus, through the alignment of the first and second viewing windows 66 and 68 with the underlying first, second, third or fourth marks 52, 54, 56 or 58, the pet owner may immediately see, and continue to see in the future, whether or not the collar is adjusted to the proper length to provide both comfort for the pet while preventing the pet from removing the collar. The pet collar 10 comprises a flexible strap 12 having a first end 16 and a second end 16 oppositely disposed from the first end 16. The pet collar 10 also has a buckle 14 having a clip 20 coupled to the first end of the flexible strap 12 and a receiver 18 coupled to the second end of the strap. The receiver 18 has a catch portion 30 removably coupleable to the clip 20 and a tension indicator portion 32 coupled to the catch portion 30 and the flexible strap second end. The tension indicator portion 32 has at least one side wall 38 with at least one position indicator (marks 52, 54, 56 or 58). A tensioning shuttle 60 is coupled for reciprocal movement along the one side wall 38. The tensioning shuttle 60 has a visual indictor (viewing window 66 or 68) alignable with the at least one position indicator (marks 52, 54, 56 or 58). A spring 62 biases the tensioning shuttle 60 in a longitudinal direction opposite to the tension upon the strap 12 through mounting the collar 10 upon a pet. The flexible strap second end is coupled to the tensioning shuttle 60. With this construction, the amount of tension of the flexible strap 12 determines the position of the tensioning shuttle 60 along the side wall 38 of the base 35.

The pet collar side wall 38 includes a first position indicator 52 alignable with a first position of the visual indicator (viewing window 66 or 68) to indicate a too loose tension of the flexible strap upon a pet. The second position indicator 54 is alignable with a second position of the visual indicator (viewing window 66 or 68) to indicate a correct tension of the flexible strap 12 upon a pet. The third position indicator 56 is alignable with a third position of the visual indicator (viewing window 66 or 68) to indicate a too tight tension of the flexible strap upon a pet.

The collar 10 also includes a fourth position indicator 58 and a second visual indicator 68. The first visual indicator 66 is alignable with the first position indicator 52 and the second visual indicator 68 is alignable with the third position indicator 56 to indicate not enough tension of the flexible strap 12 upon a pet. The first visual indicator 66 is alignable with the second position indicator 54 to indicate a correct tension of the flexible strap 12 upon a pet. The first visual indicator 66 is alignable with the third position indicator 56 and the second visual indicator 68 is alignable with the fourth position indicator 58 to indicate too much tension of the flexible strap 12 upon a pet.

The first, third and fourth position indicators 52, 56 and 58 have a first select color and the second position indicator 54 has a second select color different from the first select color. The pet collar 10 comprises a flexible strap 12 having a first end and a second end 16. The pet collar 10 also has a buckle coupling the first end to the second end, and a tension indicator portion 32 coupled to the flexible strap 12. The tension indicator portion 32 has a base 35 coupled to the flexible strap 12 and a shuttle 60 coupled to the flexible strap 12 and coupled to the base 35 for reciprocal movement relative to the base 35. The base 35 has a first tension indicator. The shuttle 60 has a second tension indicator selectively alignable with the first tension indicator to indicate the amount of tension upon the flexible strap 12. The spring 62 biases the shuttle 60 relative to the base 35 against the tension force upon the strap 12.

A pet collar 10 comprises a flexible strap 12 having a first end and a second end 16 oppositely disposed from the first end. The pet collar 10 also has a buckle 14 coupling the strap first end to the strap second end. The buckle 14 has a strap coupling portion 30 and a tension indicator portion 32. The tension indicator portion 32 has a base 35 and a sliding member 60 movably mounted to the base 35 for reciprocal, longitudinal movement. The base 35 has a plurality of longitudinally aligned visual position indicators (marks 52, 54, 56 or 58). The sliding member 60 has a tension indicator (viewing windows 66 and 68) alignable with the visual position indicators (marks 52, 54, 56 or 58). The tension indicator portion 32 also have a spring 62 biasing the sliding member 60 in a first longitudinal direction. The base 35 is coupled to the first end of the flexible strap. The sliding member 60 is coupled to the second end of the flexible strap, wherein tension upon the flexible strap places a tensioning force upon the sliding member in a second longitudinal direction opposite to the first longitudinal direction created by the spring.

It should be understood that the catch portion 30 may be of any conventional configuration, such as a single, central push down catch, a magnetic coupler, a hook and loop type fastener, or a pin and hole arrangement. The catch portion 30 may also be physically separate from the tension indicator portion 32. Also, the spring 62 may be of any conventionally know design so long as it biases the tensioning shuttle 60, such as a coil spring, leaf spring, compressible resin or material, elastic material, magnets, or the like.

It should be understood that the tensioning shuttle 60 may include a single viewing window rather than the two viewing windows shown in the preferred embodiment. The use of one viewing window would eliminate the need for four marks, as a first, second and third marks may be used in conjunction with a single window to show the three possible tension conditions described above. Also, instead of using viewing windows, the tensioning shuttle 60 may use any position element, indicator or indicating means, such as a notch, projection, pointer, or the like which is alignable with the underlying marks. Similarly, the underlying marks 52, 54, 56 and 58 is not limited to a color coding and may be any type of visual indicator, such an alphanumeric code, image, icon, pattern, design, fabric, etc. Furthermore, the positions of the visual position indicator and visual tension indicator portion may be reversed, for example, the color coding may be on the reciprocal shuttle and the viewing window or pointer may be on the stationary side wall 38. As such, the terms visual position indicator, tension indicator, and visual tension indicator portion may be interchangeable as they are both considered to be tension indicators or position indicators. Lastly, the position indicator may simply be an edge of the tensioning shuttle 60 rather than a distinct and separate component of such, as the edge of the tensioning shuttle 60 may be used against an underlying set of marks upon the base 35 to indicate its relative position thereon.

Also, it should be understood that the collar 10 may be in the form of a pet harness configured to surround the neck and/or chest of a pet.

A collar device is described herein comprising under an embodiment a housing including an emitter and a detector, wherein a base of the housing exposes the emitter and the detector. The collar device includes a spacer component comprising a plurality of optical pathways, wherein the plurality of optical pathways comprises a first optical pathway and a second optical pathway. The collar device includes the spacer component secured to the base of the housing, wherein the first optical pathway is positioned over an emitter, wherein the second optical pathway is positioned over a detector. The collar device includes the emitter configured to project light through the first optical pathway toward skin tissue of an animal. The collar device includes the detector configured to detect portions of the light reflected by the skin tissue back through the second optical pathway. The collar device includes one or more applications running on at least one processor within the housing configured to receive information of the reflected light and use the information to determine a biological metric.

The collar device of an embodiment is attachable to a collar.

The collar of an embodiment is configured to secure the collar device to the animal.

The securing the collar device creates a tension force between the collar device and the skin tissue of the animal, under an embodiment.

The tension force presses a distal end of the spacer component against the skin tissue of the animal, under an embodiment.

The plurality of optical pathways comprises open air pathways, under an embodiment.

The plurality of optical pathways comprises translucent material, under an embodiment.

The biological metric comprises a heart rate of the animal, under an embodiment.

The plurality of optical pathways comprises at least one additional optical pathway, under an embodiment.

Each additional optical pathway of the at least one additional optical pathway is positioned over a corresponding additional emitter exposed by the base of the housing, under an embodiment.

Each additional emitter is configured to project light through the corresponding additional pathway, under an embodiment.

Each additional optical pathway of the at least one additional optical pathway is positioned over a corresponding additional detector exposed by the base of the housing, under an embodiment.

Each additional detector is configured to detect portions of the light reflected by the skin tissue back through the corresponding additional pathway, under an embodiment.

The spacer component of an embodiment comprises a temperature pathway for use in detecting temperature of the animal.

The spacer component of an embodiment is non-conductive.

The temperature pathway comprises a thermal conductive probe, under an embodiment.

A proximal end of the thermal conduct probe contacts an inter-integrated circuit temperature sensor, under an embodiment.

A distal end of the thermal conduct probe contacts the animal, under an embodiment.

The temperature pathway comprises an open air temperature pathway, under an embodiment.

A proximal end of open air temperature pathway is positioned over an infrared temperature sensor, under an embodiment.

The infrared temperature sensor is configured to send infrared light through the open air temperature pathway, under an embodiment.

The spacer component of an embodiment is conductive.

A distal end of the temperature pathway terminates within the spacer component, under an embodiment.

A thermistor temperature sensor resides within the temperature pathway, under an embodiment.

The thermistor temperature sensor is coupled to the at least one processor, under an embodiment.

A thermal contact probe is seated in a recess of the spacer component, under an embodiment.

A proximal end of the thermal conduct probe contacts an inter-integrated circuit temperature sensor, under an embodiment.

The detector is a photodiode, under an embodiment.

The emitter is a light emitting diode, under an embodiment.

Computer networks suitable for use with the embodiments described herein include local area networks (LAN), wide area networks (WAN), Internet, or other connection services and network variations such as the world wide web, the public internet, a private internet, a private computer network, a public network, a mobile network, a cellular network, a value-added network, and the like. Computing devices coupled or connected to the network may be any microprocessor controlled device that permits access to the network, including terminal devices, such as personal computers, workstations, servers, mini computers, main-frame computers, laptop computers, mobile computers, palm top computers, hand held computers, mobile phones, TV set-top boxes, or combinations thereof. The computer network may include one of more LANs, WANs, Internets, and computers. The computers may serve as servers, clients, or a combination thereof.

The system and apparatus for measurement of physiological data can be a component of a single system, multiple systems, and/or geographically separate systems. The system and apparatus for measurement of physiological data can also be a subcomponent or subsystem of a single system, multiple systems, and/or geographically separate systems. The components of system and apparatus for measurement of physiological data can be coupled to one or more other components (not shown) of a host system or a system coupled to the host system.

One or more components of the system and apparatus for measurement of physiological data and/or a corresponding interface, system or application to which the system and apparatus for measurement of physiological data is coupled or connected includes and/or runs under and/or in association with a processing system. The processing system includes any collection of processor-based devices or computing devices operating together, or components of processing systems or devices, as is known in the art. For example, the processing system can include one or more of a portable computer, portable communication device operating in a communication network, and/or a network server. The portable computer can be any of a number and/or combination of devices selected from among personal computers, personal digital assistants, portable computing devices, and portable communication devices, but is not so limited. The processing system can include components within a larger computer system.

The processing system of an embodiment includes at least one processor and at least one memory device or subsystem. The processing system can also include or be coupled to at least one database. The term "processor" as generally used herein refers to any logic processing unit, such as one or more central processing units (CPUs), digital signal processors (DSPs), application-specific integrated circuits (ASIC), etc. The processor and memory can be monolithically integrated onto a single chip, distributed among a number of chips or components, and/or provided by some combination of algorithms. The methods described herein can be implemented in one or more of software algorithm(s), programs, firmware, hardware, components, circuitry, in any combination.

The components of any system that include the system and apparatus for measurement of physiological data can be located together or in separate locations. Communication paths couple the components and include any medium for communicating or transferring files among the components. The communication paths include wireless connections, wired connections, and hybrid wireless/wired connections. The communication paths also include couplings or connections to networks including local area networks (LANs), metropolitan area networks (MANs), wide area networks (WANs), proprietary networks, interoffice or backend networks, and the Internet. Furthermore, the communication paths include removable fixed mediums like floppy disks, hard disk drives, and CD-ROM disks, as well as flash RAM, Universal Serial Bus (USB) connections, RS-232 connections, telephone lines, buses, and electronic mail messages.

Aspects of the system and apparatus for measurement of physiological data and corresponding systems and methods described herein may be implemented as functionality programmed into any of a variety of circuitry, including programmable logic devices (PLDs), such as field programmable gate arrays (FPGAs), programmable array logic (PAL) devices, electrically programmable logic and memory devices and standard cell-based devices, as well as application specific integrated circuits (ASICs). Some other possibilities for implementing aspects of the system and apparatus for measurement of physiological data and corresponding systems and methods include: microcontrollers with memory (such as electronically erasable programmable read only memory (EEPROM)), embedded microprocessors, firmware, software, etc. Furthermore, aspects of the system and apparatus for measurement of physiological data and corresponding systems and methods may be embodied in microprocessors having software-based circuit emulation, discrete logic (sequential and combinatorial), custom devices, fuzzy (neural) logic, quantum devices, and hybrids of any of the above device types. Of course the underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, etc.

It should be noted that any system, method, and/or other components disclosed herein may be described using computer aided design tools and expressed (or represented), as data and/or instructions embodied in various computer-readable media, in terms of their behavioral, register transfer, logic component, transistor, layout geometries, and/or other characteristics. Computer-readable media in which such formatted data and/or instructions may be embodied include, but are not limited to, non-volatile storage media in various forms (e.g., optical, magnetic or semiconductor storage media) and carrier waves that may be used to transfer such formatted data and/or instructions through wireless, optical, or wired signaling media or any combination thereof. Examples of transfers of such formatted data and/or instructions by carrier waves include, but are not limited to, transfers (uploads, downloads, e-mail, etc.) over the Internet and/or other computer networks via one or more data transfer protocols (e.g., HTTP, FTP, SMTP, etc.). When received within a computer system via one or more computer-readable media, such data and/or instruction-based expressions of the above described components may be processed by a processing entity (e.g., one or more processors) within the computer system in conjunction with execution of one or more other computer programs.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import, when used in this application, refer to this application as a whole and not to any particular portions of this application. When the word "or" is used in reference to a list of two or more items, that word covers all of the following interpretations of the word: any of the items in the list, all of the items in the list and any combination of the items in the list.

The above description of embodiments of the system and apparatus for measurement of physiological data is not intended to be exhaustive or to limit the systems and methods to the precise forms disclosed. While specific embodiments of, and examples for, the system and apparatus for measurement of physiological data and corresponding systems and methods are described herein for illustrative purposes, various equivalent modifications are possible within the scope of the systems and methods, as those skilled in the relevant art will recognize. The teachings of the system and apparatus for measurement of physiological data and corresponding systems and methods provided herein can be applied to other systems and methods, not only for the systems and methods described above.

The elements and acts of the various embodiments described above can be combined to provide further embodiments. These and other changes can be made to the system and apparatus for measurement of physiological data and corresponding systems and methods in light of the above detailed description.

What is claimed is:

1. A collar device comprising,
   a housing including an emitter and a detector, wherein a base of the housing has an opening that exposes the emitter and the detector;
   a spacer component separate from the housing, the spacer component comprising a plurality of optical pathway elements, wherein the plurality of optical pathway elements comprises a first optical pathway element and a second optical pathway element;
   the spacer component secured to the base of the housing and positioned to extend through the opening of the housing and protrude outwardly from the housing, wherein the first optical pathway element is positioned over and in contact with an emitter, wherein the second optical pathway element is positioned over and in contact with a detector;
   the emitter configured to project light through the first optical pathway element toward skin tissue of an animal;
   the detector configured to detect portions of the light reflected by the skin tissue back through the second optical pathway element;
   one or more applications running on at least one processor within the housing configured to receive information of the reflected light and use the information to determine a biological metric.

2. The collar device of claim 1, wherein the collar device is attachable to a collar.

3. The collar device of claim 2, wherein the collar is configured to secure the collar device to the animal.

4. The collar device of claim 3, wherein the securing the collar device creates a tension force between the collar device and the skin tissue of the animal.

5. The collar device of claim 4, wherein the tension force presses a distal end of the spacer component against the skin tissue of the animal.

6. The collar device of claim 1, wherein the plurality of optical pathway elements comprises translucent material.

7. The collar device of claim 1, wherein the biological metric comprises a heart rate of the animal.

8. The collar device of claim 1, wherein the plurality of optical pathway elements comprises at least one additional optical pathway element.

9. The collar device of claim 8, wherein each additional optical pathway element of the at least one additional optical pathway element is positioned over a corresponding additional emitter exposed by the base of the housing.

10. The collar device of claim 9, wherein each additional emitter is configured to project light through the corresponding additional pathway element.

11. The collar device of claim 8, wherein each additional optical pathway element of the at least one additional optical pathway element is positioned over a corresponding additional detector exposed by the base of the housing.

12. The collar device of claim 11, wherein each additional detector is configured to detect portions of the light reflected by the skin tissue back through the corresponding additional pathway element.

13. The collar device of claim 1, wherein the spacer component comprises a temperature pathway element for use in detecting temperature of the animal.

14. The collar device of claim 13, wherein the spacer component is thermally non-conductive.

15. The collar device of claim 14, wherein the temperature pathway element comprises a thermal conductive probe.

16. The collar device of claim 15, wherein a proximal end of the thermal conduct probe contacts an inter-integrated circuit temperature sensor.

17. The collar device of claim 16, wherein a distal end of the thermal conduct probe contacts the animal.

18. The collar device of claim 13, wherein the spacer component is thermally conductive.

19. The collar device of claim 18, wherein a distal end of the temperature pathway element terminates within the spacer component.

20. The collar device of claim 19, wherein a thermistor temperature sensor resides within the temperature pathway element.

21. The collar device of claim 20, wherein the thermistor temperature sensor is coupled to the at least one processor.

22. The collar device of claim 18, wherein a thermal contact probe is seated in a recess of the spacer component.

23. The collar device of claim 22, wherein a proximal end of the thermal conduct probe contacts an inter-integrated circuit temperature sensor.

24. The collar device of claim 1, wherein the detector is a photodiode.

25. The collar device of claim 1, wherein the emitter is a light emitting diode.

\* \* \* \* \*